US008685391B2

(12) United States Patent
Marini

(10) Patent No.: US 8,685,391 B2
(45) Date of Patent: *Apr. 1, 2014

(54) SKIN CARE COMPOSITIONS

(75) Inventor: Jan Marini, San Jose, CA (US)

(73) Assignee: Jan Marini Skin Research, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/605,883

(22) Filed: Sep. 6, 2012

(65) Prior Publication Data

US 2013/0171119 A1 Jul. 4, 2013

Related U.S. Application Data

(63) Continuation of application No. 12/167,094, filed on Jul. 2, 2008, now Pat. No. 8,283,314.

(60) Provisional application No. 60/947,607, filed on Jul. 2, 2007.

(51) Int. Cl.
*A61K 38/43* (2006.01)

(52) U.S. Cl.
USPC ............ 424/94.1; 514/1.1; 514/7.6; 514/8.9; 514/9.2; 514/18.6; 514/690

(58) Field of Classification Search
None
See application file for complete search history.

(56) References Cited

U.S. PATENT DOCUMENTS

| | | | |
|---|---|---|---|
| 4,837,019 | A | 6/1989 | Georgalas et al. |
| 5,583,016 | A | 12/1996 | Villeponteau et al. |
| 5,618,544 | A | 4/1997 | Brown |
| 5,753,214 | A | 5/1998 | Yoshioka et al. |
| 6,277,892 | B1 | 8/2001 | Deckner et al. |
| 6,355,261 | B1 | 3/2002 | Bonda et al. |
| 6,492,326 | B1 | 12/2002 | Robinson et al. |
| 6,756,045 | B1 | 6/2004 | Neudecker et al. |
| 6,974,799 | B2 | 12/2005 | Lintner |
| 7,279,328 | B1 | 10/2007 | Andrews et al. |
| 8,283,314 | B1 | 10/2012 | Marini |
| 2004/0042996 | A1 | 3/2004 | Pauly et al. |
| 2004/0180020 | A1 | 9/2004 | Manelski et al. |
| 2005/0142095 | A1 | 6/2005 | Scancarella et al. |
| 2005/0152857 | A1 | 7/2005 | DiNardo et al. |
| 2005/0175559 | A1 | 8/2005 | DiNardo et al. |
| 2005/0197407 | A1 | 9/2005 | DiNardo et al. |
| 2006/0258562 | A1 | 11/2006 | Tennenbaum |

OTHER PUBLICATIONS

Botchkina et al., International Journal of Cosmetics Science, 2004, vol. 26, p. 103-104.*
Smith et al., Journal of the American Academy of Dermatology, 1996, vol. 35, No. 3, p. 388-391.*
Search results, May 28, 2013, 2 page PDF.*
Boukamp, P. Ageing mechanisms: the role of telomere loss. Clin Exp Dermatol. 2001; 26(7): 562-565.
Botchkina et al. Telomere loss and skin aging. International Journal of Cosmetic Science. 2004; 26(2): 103-4.
Christian Dior. Capture First Action face cream press release. European Cosmetic Markets. Feb. 2004.
Fitzpatrick, et al. Reversal of photodamage with topical growth factors: a pilot study. J Cosmetic & laser. 2003; 5:25-34.
Jurkiewicz, et al. Effect of topically applied tocopherol on ultraviolet radiation-mediated free radical damage in skin. J Invest Dermatol. Apr. 1995;104(4):484-8.
Katiyar. Skin photoprotection by green tea: antioxidant and immunomodulatory effects. Curr Drug Targets Immune Endocr Metabol Disord. 2003; 3(3):234-42. Abstract only.
MailOnline. Could stem cell cream be future of face care? Available at http://www.dailymail.co.uk/femail/article-443115/Could-stem-cell-cream-future-face-care.html. Accessed Aug. 11, 2011.
McDaniel, et al. Clinical efficacy assessment in photodamaged skin of 0.5% and 1.0% idebenone. Journal of Cosmetic Dermatology. 2005; 4: 167-73.
ReVive Skincare. Peau magnifique youth recruit. Available at http://www.reviveskincare.com/store/shop/Serums_Peau-Magnifique-Youth-Recruit_prod120041. Accessed Aug. 11, 2011.
Telomerase-Nanoparticle Delivery for Anti-Aging Applications, a Sponsored Research Proposal, published Jan. 16, 2007 as part of Telomolecular Corporation SB-2 filing with the SEC, accession No. 1353532-7-3. Appendix EX-4.
Theoret, et al. Update on wound repair. Clin Tech Equine Pract. 2004; 3:110-122.
Veuillez, et al. Synthesis and characterization of an acylated dipeptide (Myr-Trp-Leu) with modified transmucosal transport properties. Eur J Pharm Biopharm. Jul. 1999;48(1):21-6.

* cited by examiner

*Primary Examiner* — Kade Ariani
(74) *Attorney, Agent, or Firm* — Wilson Sonsini Goodrich & Rosati

(57) ABSTRACT

Dermatological and cosmetic compositions and methods are provided to reduce the appearance of biological and/or environmentally-caused aging.

10 Claims, No Drawings

US 8,685,391 B2

SKIN CARE COMPOSITIONS

CROSS-REFERENCE

This application is a continuation application which claims the benefit of U.S. application Ser. No. 12/167,094, filed Jul. 2, 2008; which claims the benefit of U.S. Provisional Application No. 60/947,607, filed Jul. 2, 2007, both of which applications are incorporated herein by reference in their entirety.

BACKGROUND OF THE INVENTION

Maintaining a youthful appearance is of great importance to many people. There is a need for treatments designed to extend or promote the youthful appearance of skin.

SUMMARY OF THE INVENTION

One aspect of the present invention is dermatological and cosmetic compositions that help to reduce the appearance of biological and/or environmentally-caused aging comprising: a reverse transcriptase component of telomerase; one or more growth factors; at least two acylated peptides; and optionally, at least one skin benefit agent selected from the group consisting of antioxidants, humectants and moisturizing agents.

A second aspect of the invention is cosmetic or dermatological compositions comprising: an inhibitor of a component of telomerase; one or more growth factors; at least two acylated peptides; and optionally, at least one skin benefit agent selected from the group consisting of antioxidants, humectants and moisturizing agents.

A third aspect of the invention is cosmetic or dermatological compositions comprising: a reverse transcriptase component of a telomerase; an Epidermal Growth Factor; a Keratinocyte Growth Factor; a Transforming Growth Factor-β1; at least one myristoylated peptide; at least one antioxidant; at least one humectant or moisturizing agent; and a cosmetically suitable vehicle.

A fourth aspect of the invention is cosmetic or dermatological compositions comprising: a reverse transcriptase component of a telomerase; a Vascular Endothelial Growth Factor; a Keratinocyte Growth Factor; a Transforming Growth Factor-β1; at least one myristoylated peptide; at least one antioxidant; at least one humectant or moisturizing agent; and a cosmetically suitable vehicle.

A fifth aspect of the invention is cosmetic or dermatological compositions comprising: an inhibitor of a component of a telomerase; an Epidermal Growth Factor; a Keratinocyte Growth Factor; a Transforming Growth Factor-β1; at least one myristoylated peptide; at least one antioxidant; at least one humectant or moisturizing agent; and a cosmetically suitable vehicle.

A sixth aspect of the invention is cosmetic or dermatological compositions comprising: an inhibitor of a component of a telomerase; a Vascular Endothelial Growth Factor; a Keratinocyte Growth Factor; a Transforming Growth Factor-β1; at least one myristoylated peptide; at least one antioxidant; at least one humectant or moisturizing agent; and a cosmetically suitable vehicle.

Another aspect of the invention provides methods for improving the appearance of skin comprising applying topically to the skin a composition comprising: a reverse transcriptase component of a telomerase; one or more growth factors; at least two acylated peptides; and optionally, at least one skin benefit agent selected from the group consisting of antioxidants, and humectants and moisturizing agents.

A further aspect of the invention provides methods for improving the appearance of skin comprising applying topically to the skin a composition comprising: an inhibitor to a component of a telomerase; one or more growth factors; at least two acylated peptides; and optionally, at least one skin benefit agent selected from the group consisting of antioxidants, humectants and moisturizing agents.

In some embodiments of the invention, the composition further comprises an RNA component of telomerase.

In some embodiments of the invention, the reverse transcriptase component of telomerase has an amino acid sequence with at least 90%, 95%, 98%, or 99% sequence homology to the amino acid sequence of a telomerase reverse transcriptase of an animal. In other embodiments of the invention, the RNA component of telomerase has an amino acid sequence with at least 90%, 95%, 98%, or 99% sequence homology to the amino acid sequence of a telomerase RNA of an animal. In yet other embodiments of the present invention the RNA component of telomerase has an amino acid sequence with at least 90%, 95%, 98%, or 99% sequence homology to the amino acid sequence of human telomerase RNA (hTR). In other embodiments of the present invention, the reverse transcriptase component of telomerase has an amino acid sequence with at least 90%, 95%, 98%, or 99% sequence homology to the amino acid sequence of a human telomerase reverse transcriptase (hTRT). In other embodiments of the present invention, the RNA component of telomerase comprises human telomerase RNA (hTR). In other embodiments of the present invention, the reverse transcriptase component of telomerase comprises human telomerase reverse transcriptase (hTRT). In some embodiments of the invention the compositions comprise a telomerase reverse transcriptase and a telomerase RNA. In some of the embodiments of the invention, the telomerase reverse transcriptase is recombinant telomerase reverse transcriptase. In some of the embodiments of the invention, the telomerase RNA is recombinant telomerase RNA.

In some embodiments of the invention, the inhibitor of a component of telomerase is an antibody. In some embodiments of the invention, the antibody to a component of telomerase has an amino acid sequence with at least 90%, 95%, 98%, or 99% sequence homology to the amino acid sequence of an antibody to a component of animal telomerase. In other embodiments of the invention, the antibody to a component of telomerase has an amino acid sequence with at least 90%, 95%, 98%, or 99% sequence homology to the amino acid sequence of an antibody to a component of human telomerase. In some embodiments of the invention, the antibody comprises a human telomerase RNA (hTR) antibody. In other embodiments of the invention, the antibody to telomerase comprises a human telomerase reverse transcriptase (hTRT) antibody.

In some embodiments of the invention, the one or more growth factors comprise an Epidermal Growth Factor. In other embodiments of the invention, the Epidermal Growth Factor is a human Epidermal Growth Factor. In some embodiments of the invention, the one or more growth factors comprise a Vascular Endothelial Growth Factor. In some embodiments of the invention, the one or more growth factors comprise human endothelial growth factor. In some embodiments of the invention, the one or more growth factors comprise one or more Fibroblast Growth Factors. In some embodiments of the invention, the one or more growth factors comprise a Keratinocyte Growth Factor. In some embodiments of the invention, the one or more growth factors comprise a human Keratinocyte Growth Factor. In some embodiments of the invention, the one or more growth factors comprise KGF-1. In other embodiments of the invention, the one or more growth factors comprise KGF-2. In some embodiments of the invention, the one or more growth factors comprise Transforming Growth Factor-β1. In some embodiments of the invention, the one or more growth factors comprise a human Transforming Growth Factor-β1. In some embodiments of the invention, the one or more growth factors comprise Vascular Endothelial Growth Factor. In some embodiments of the invention, the one or more growth factors comprise a human Vascular Endothelial Growth Factor. In some embodiments of the invention, the one or more growth factors is one or more recombinant growth factors.

In some embodiments of the invention, the at least two acylated peptides comprise a first acylated peptide which is myristoylated. In some embodiments of the invention, the at least two acylated peptides comprise a second acylated peptide which is myristoylated. In some embodiments of the invention, the at least two acylated peptides comprise a first acylated peptide which is myristoylated and a second acylated peptide which is palmitoylated. In some embodiments of the invention, the at least two acylated peptides comprise a third acylated peptide and optionally four or more acylated peptides.

In some embodiments of the invention, the compositions comprise at least one antioxidant, independently chosen from the group consisting of ascorbic acid and its salts, ascorbyl esters of fatty acids, ascorbic acid derivatives (e.g., magnesium ascorbyl phosphate, sodium ascorbyl phosphate, ascorbyl sorbate), tocopherol, tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters (e.g., propyl gallate), nordihydroguaiaretic acid, bioflavonoids, quinones, and ubiquinones including Coenzyme Q and its derivatives. In some embodiments of the invention, the composition comprises a green tea extract. In some embodiments of the invention, the at least one antioxidant is ubiquinone. In some embodiments of the invention, the at least one antioxidant is green tea extract. In some embodiments of the invention, the at least one antioxidant is tocopherol acetate.

In some embodiments of the invention, the composition, one or more humectants are selected from the group consisting of D,L-panthenol, D-panthenol, sodium hyaluronate, methylsilanol mannuronate and butylene glycol.

In some embodiments, Telomerase RNA is present in compositions of the present invention at concentrations of at least from about 0.000001% w/w to about 0.01% w/w. In some embodiments, Telomerase RNA is present in compositions of the present invention at concentrations of at least from about 0.000005% w/w to about 0.005% w/w. In some embodiments, Telomerase RNA is present in compositions of the present invention at concentrations of at least from about 0.00001% w/w to about 0.001% w/w. In some embodiments, Telomerase RNA is present in compositions of the present invention at concentrations of at least from about 0.00005% w/w to about 0.001% w/w. In some embodiments, Telomerase RNA is present in compositions of the present invention at concentrations of at least from about 0.0001% w/w to about 0.001% w/w. In some embodiments, Telomerase RNA is present in compositions of the present invention at concentrations of more than about 0.000006% w/w. In some embodiments, Telomerase RNA is present in compositions of the present invention at concentrations of more than about 0.00006% w/w. In some embodiments, Telomerase RNA is present in compositions of the present invention at concentrations of more than about 0.0006% w/w. In some embodiments, Telomerase RNA is present in compositions of the present invention at concentrations of more than about 0.005% w/w. In some embodiments, Telomerase RNA is present in compositions of the present invention at concentrations of more than about 0.006% w/w. In some embodiments, Telomerase RNA is present in compositions of the present invention at concentrations of more than about 0.01% w/w. In some embodiments, Telomerase RNA is present in compositions of the present invention at concentrations of less than about 0.01% w/w. In some embodiments, Telomerase RNA is present in compositions of the present invention at concentrations of less than about 0.001% w/w. In some embodiments, Telomerase RNA is present in compositions of the present invention at concentrations of less than about 0.0007% w/w. In some embodiments, Telomerase RNA is present in compositions of the present invention at concentrations of less than about 0.0006% w/w. In some embodiments, Telomerase RNA is present in compositions of the present invention at concentrations of less than about 0.0001% w/w.

In some embodiments, Telomerase reverse transcriptase (RT) is present in compositions of the present invention at concentrations of at least from about 0.000001% w/w to about 0.01% w/w. In some embodiments, Telomerase reverse transcriptase (RT) is present in compositions of the present invention at concentrations of at least from about 0.000005% w/w to about 0.005% w/w. In some embodiments, Telomerase reverse transcriptase (RT) is present in compositions of the present invention at concentrations of at least from about 0.00001% w/w to about 0.001% w/w. In some embodiments, Telomerase reverse transcriptase (RT) is present in compositions of the present invention at concentrations of at least from about 0.00005% w/w to about 0.001% w/w. In some embodiments, Telomerase reverse transcriptase (RT) is present in compositions of the present invention at concentrations of at least from about 0.0001% w/w to about 0.001% w/w. In some embodiments, Telomerase reverse transcriptase (RT) is present in compositions of the present invention at concentrations of more than about 0.000006% w/w. In some embodiments, Telomerase reverse transcriptase (RT) is present in compositions of the present invention at concentrations of more than about 0.00006% w/w. In some embodiments, Telomerase reverse transcriptase (RT) is present in compositions of the present invention at concentrations of more than about 0.0005% w/w. In some embodiments, Telomerase reverse transcriptase (RT) is present in compositions of the present invention at concentrations of more than about 0.0006% w/w. In some embodiments, Telomerase reverse transcriptase (RT) is present in compositions of the present invention at concentrations of more than about 0.006% w/w. In some embodiments, Telomerase reverse transcriptase (RT) is present in compositions of the present invention at concentrations of less than about 0.01% w/w. In some embodiments, Telomerase reverse transcriptase (RT) is present in compositions of the present invention at concentrations of less than about 0.006% w/w. In some embodiments, Telomerase reverse transcriptase (RT) is present in compositions of the present invention at concentrations of less than about 0.001% w/w. In some embodiments, Telomerase reverse transcriptase (RT) is present in compositions of the present invention at concentrations of less than about 0.0007% w/w. In some embodiments, Telomerase reverse transcriptase (RT) is present in compositions of the present invention at concentrations of less than about 0.0006% w/w. In some embodiments, Telomerase reverse transcriptase (RT) is present in compositions of the present invention at concentrations of less than about 0.0001% w/w. In some embodiments, Telomerase reverse transcriptase (RT) is present in compositions of the present invention at concentrations of less than about 0.00007% w/w. In some embodiments, Telomerase reverse transcriptase (RT) is present in compositions of the present invention at concentrations of less than about 0.00006% w/w. In some embodiments, Telomerase reverse transcriptase (RT) is present in compositions of the present invention at concentrations of less than about 0.00001% w/w. In some embodiments, Telomerase reverse transcriptase (RT) is present in compositions of the present invention at concentrations of less than about 0.000006% w/w.

In some embodiments, antibody to Telomerase RT is present in compositions of the present invention at concentrations of at least from about 0.000001% w/w to about 0.01% w/w. In some embodiments, antibody to Telomerase RT is present in compositions of the present invention at concentrations of at least from about 0.000005% w/w to about 0.005% w/w. In some embodiments, antibody to Telomerase RT is present in compositions of the present invention at concentrations of at least from about 0.00001% w/w to about 0.001% w/w. In some embodiments, antibody to Telomerase RT is present in compositions of the present invention at concentrations of at least from about 0.00005% w/w to about 0.001% w/w. In some embodiments, antibody to Telomerase RT is present in compositions of the present invention at concentrations of at least from about 0.0001% w/w to about 0.001% w/w. In some embodiments, antibody to Telomerase RT is present in compositions of the present invention at concentrations of more than about 0.000001% w/w. In some embodiments, antibody to Telomerase RT is present in compositions of the present invention at concentrations of more than about 0.000006% w/w. In some embodiments, antibody to Telomerase RT is present in compositions of the present invention at concentrations of more than about 0.00001% w/w. In some embodiments, antibody to Telomerase RT is present in compositions of the present invention at concentrations of more than about 0.00005% w/w. In some embodiments, antibody to Telomerase RT is present in compositions of the present invention at concentrations of more than about 0.00006% w/w. In some embodiments, antibody to Telomerase RT is present in compositions of the present invention at concentrations of more than about 0.0001% w/w. In some embodiments, antibody to Telomerase RT is present in compositions of the present invention at concentrations of more than about 0.0006% w/w. In some embodiments, antibody to Telomerase RT is present in compositions of the present invention at concentrations of less than about 0.01% w/w. In some embodiments, antibody to Telomerase RT is present in compositions of the present invention at concentrations of less than about 0.006% w/w. In some embodiments, antibody to Telomerase RT is present in compositions of the present invention at concentrations of less than about 0.003% w/w. In some embodiments, antibody to Telomerase RT is present in compositions of the present invention at concentrations of less than about 0.001% w/w. In some embodiments, antibody to Telomerase RT is present in compositions of the present invention at concentrations of less than about 0.0007% w/w. In some embodiments, antibody to Telomerase RT is present in compositions of the present invention at concentrations of less than about 0.0006% w/w. In some embodiments, antibody to Telomerase RT is present in compositions of the present invention at concentrations of less than about 0.0001% w/w. In some embodiments, antibody to Telomerase RT is present in compositions of the present invention at concentrations of less than about 0.00006% w/w. In some embodiments, antibody to Telomerase RT is present in compositions of the present invention at concentrations of less than about 0.00001% w/w. In some embodiments, antibody to Telomerase RT is present in compositions of the present invention at concentrations of less than about 0.000007% w/w. In some embodiments, antibody to Telomerase RT is present in compositions of the present invention at concentrations of less than about 0.000006% w/w. In some embodiments, antibody to Telomerase RT is present in compositions of the present invention at concentrations of less than about 0.000001% w/w.

In some embodiments, Epidermal Growth Factor is present in compositions of the present invention at concentrations of at least from about 0.000001% w/w to about 0.001% w/w. In some embodiments, Epidermal Growth Factor is present in compositions of the present invention at concentrations of at least from about 0.000001% w/w to about 0.0005% w/w. In some embodiments, Epidermal Growth Factor is present in compositions of the present invention at concentrations of at least from about 0.000001% w/w to about 0.0001% w/w. In some embodiments, Epidermal Growth Factor is present in compositions of the present invention at concentrations of at least from about at least from about 0.00001% w/w to about 0.005% w/w. In some embodiments, Epidermal Growth Factor is present in compositions of the present invention at concentrations of at least about 0.000001% w/w. In some embodiments, Epidermal Growth Factor is present in compositions of the present invention at concentrations of at least about 0.0000015% w/w. In some embodiments, Epidermal Growth Factor is present in compositions of the present invention at concentrations of at least about 0.0000065% w/w. In some embodiments, Epidermal Growth Factor is present in compositions of the present invention at concentrations of at least about 0.000015% w/w. In some embodiments, Epidermal Growth Factor is present in compositions of the present invention at concentrations of at least about 0.000065% w/w. In some embodiments, Epidermal Growth Factor is present in compositions of the present invention at concentrations of at least about 0.00015% w/w. In some embodiments, Epidermal Growth Factor is present in compositions of the present invention at concentrations of at least about 0.00065% w/w. In some embodiments, Epidermal Growth Factor is present in compositions of the present invention at concentrations of at least about 0.001% w/w. In some embodiments, Epidermal Growth Factor is present in compositions of the present invention at concentrations of less than about 0.001% w/w. In some embodiments, Epidermal Growth Factor is present in compositions of the present invention at concentrations of less than about 0.00065% w/w. In some embodiments, Epidermal Growth Factor is present in compositions of the present invention at concentrations of less than about 0.0005% w/w. In some embodiments, Epidermal Growth Factor is present in compositions of the present invention at concentrations of less than about 0.00015% w/w. In some embodiments, Epidermal Growth Factor is present in compositions of the present invention at concentrations of less than about 0.000065% w/w. In some embodiments, Epidermal Growth Factor is present in compositions of the present invention at concentrations of less than about 0.000015 w/w.

In some embodiments, Vascular Endothelial Growth Factor is present in compositions of the present invention at concentrations of at least from about 0.000001% w/w to about 0.001% w/w. In some embodiments, Vascular Endothelial Growth Factor is present in compositions of the present invention at concentrations of at least from about 0.000001% w/w to about 0.0005% w/w. In some embodiments, Vascular Endothelial Growth Factor is present in compositions of the present invention at concentrations of at least from about 0.000001% w/w to about 0.0001% w/w. In some embodiments, Vascular Endothelial Growth Factor is present in compositions of the present invention at concentrations of at least from about 0.000001% w/w to about 0.001% w/w. In some embodiments, Vascular Endothelial Growth Factor is present in compositions of the present invention at concentrations of at least about 0.000001% w/w. In some embodiments, Vascular Endothelial Growth Factor is present in compositions of the present invention at concentrations of at least about 0.0000015% w/w. In some embodiments, Vascular Endothelial Growth Factor is present in compositions of the present invention at concentrations of at least about 0.0000065% w/w. In some embodiments, Vascular Endothelial Growth Factor is present in compositions of the present invention at concentrations of at least about 0.00001% w/w. In some embodiments, Vascular Endothelial Growth Factor is present in compositions of the present invention at concentrations of at least about 0.000015% w/w. In some embodiments, Vascular Endothelial Growth Factor is present in compositions of the present invention at concentrations of at least about 0.00006% w/w. In some embodiments, Vascular Endothelial Growth Factor is present in compositions of the present invention at concentrations of at least about 0.000065% w/w. In some embodiments, Vascular Endothelial Growth Factor is present in compositions of the present invention at concentrations of at least about 0.0001% w/w. In some embodiments, Vascular Endothelial Growth Factor is present in compositions of the present invention at concentrations of at least about 0.00015% w/w. In some embodiments, Vascular Endothelial Growth Factor is present in compositions of the present invention at concentrations of at least about 0.0006% w/w. In some embodiments, Vascular Endothelial Growth Factor is present in compositions of the present invention at concentrations of at least about 0.00065% w/w. In some embodiments, Vascular Endothelial Growth Factor is present in compositions of the present invention at concentrations of at least about 0.001% w/w. In some embodiments, Vascular Endothelial Growth Factor is present in compositions of the present invention at concentrations of less than about 0.001% w/w. In some embodiments, Vascular Endothelial Growth Factor is present in compositions of the present invention at concentrations of less than about 0.0007% w/w. In some embodiments, Vascular Endothelial Growth Factor is present in compositions of the present invention at concentrations of less than about 0.00065% w/w. In some embodiments, Vascular Endothelial Growth Factor is present in compositions of the present invention at concentrations of less than about 0.0002% w/w. In some embodiments, Vascular Endothelial Growth Factor is present in compositions of the present invention at concentrations of less than about 0.00015% w/w. In some embodiments, Vascular Endothelial Growth Factor is present in compositions of the present invention at concentrations of less than about 0.000065% w/w. In some embodiments, Vascular Endothelial Growth Factor is present in compositions of the present invention at concentrations of less than about 0.000015% w/w. In some embodiments, Vascular Endothelial Growth Factor is present in compositions of the present invention at concentrations of less than about 0.000007% w/w. In some embodiments, Vascular Endothelial Growth Factor is present in compositions of the present invention at concentrations of less than about 0.000001% w/w.

In some embodiments of the invention, a Fibroblast Growth Factor is present in the compositions of the present invention at concentrations of at least from about 0.000001% w/w to about 0.01% w/w. In some embodiments of the invention, a Fibroblast Growth Factor is present in the compositions of the present invention at concentrations of at least from about 0.000001% w/w to about 0.001% w/w. In some embodiments of the invention, a Fibroblast Growth Factor is present in the compositions of the present invention at concentrations of at least from about 0.000001% w/w to about 0.0001% w/w. In some embodiments of the invention, a Fibroblast Growth Factor is present in the compositions of the present invention at concentrations of at least about 0.000001% w/w. In some embodiments of the invention, a Fibroblast Growth Factor is present in the compositions of the present invention at concentrations of at least about 0.000002% w/w. In some embodiments of the invention, a Fibroblast Growth Factor is present in the compositions of the present invention at concentrations of at least about 0.000003% w/w. In some embodiments of the invention, a Fibroblast Growth Factor is present in the compositions of the present invention at concentrations of at least about 0.000004% w/w. In some embodiments of the invention, a Fibroblast Growth Factor is present in the compositions of the present invention at concentrations of at least about 0.000005% w/w. In some embodiments of the invention, a Fibroblast Growth Factor is present in the compositions of the present invention at concentrations of at least about 0.000006% w/w. In some embodiments of the invention, a Fibroblast Growth Factor is present in the compositions of the present invention at concentrations of at least about 0.00001% w/w. In some embodiments of the invention, a Fibroblast Growth Factor is present in the compositions of the present invention at concentrations of at least about 0.00002% w/w. In some embodiments of the invention, a Fibroblast Growth Factor is present in the compositions of the present invention at concentrations of at least about 0.00003% w/w. In some embodiments of the invention, a Fibroblast Growth Factor is present in the compositions of the present invention at concentrations of at least about 0.00004% w/w. In some embodiments of the invention, a Fibroblast Growth Factor is present in the compositions of the present invention at concentrations of at least about 0.00005% w/w. In some embodiments of the invention, a Fibroblast Growth Factor is present in the compositions of the present invention at concentrations of at least about 0.00006% w/w. In some embodiments of the invention, a Fibroblast Growth Factor is present in the compositions of the present invention at concentrations of at least about 0.00007% w/w. In some embodiments of the invention, a Fibroblast Growth Factor is present in the compositions of the present invention at concentrations of at least about 0.0001% w/w. In some embodiments of the invention, a Fibroblast Growth Factor is present in the compositions of the present invention at concentrations of at least about 0.0003% w/w. In some embodiments of the invention, a Fibroblast Growth Factor is present in the compositions of the present invention at concentrations of at least about 0.0006% w/w. In some embodiments of the invention, a Fibroblast Growth Factor is present in the compositions of the present invention at concentrations of at least about 0.001% w/w. In some embodiments of the invention, a Fibroblast Growth Factor is present in the compositions at concentrations less than about 0.01% w/w. In some embodiments of the invention, a Fibroblast Growth Factor is present in the compositions at concentrations less than about 0.006% w/w. In some embodiments of the invention, a Fibroblast Growth Factor is present in the compositions at concentrations less than about 0.001% w/w. In some embodiments of the invention, a Fibroblast Growth Factor is present in the compositions at concentrations less than about 0.0007% w/w. In some embodiments of the invention, a Fibroblast Growth Factor is present in the compositions at concentrations less than about 0.00065% w/w. In some embodiments of the invention, a Fibroblast Growth Factor is present in the compositions at concentrations less than about 0.0006% w/w. 0. In some embodiments of the invention, a Fibroblast Growth Factor is present in the compositions at concentrations less than about 0.00010% w/w. In some embodiments of the invention, a Fibroblast Growth Factor is present in the compositions at concentrations less than about 0.00007% w/w. In some embodiments of the invention, a Fibroblast Growth Factor is present in the compositions at concentrations less than about 0.00006% w/w In some embodiments of the invention, a Fibroblast Growth Factor is present in the compositions at concentrations less than about 0.00001% w/w. In some embodiments of the invention, a Fibroblast Growth Factor is present in the compositions at concentrations less than about 0.000007% w/w. In some embodiments of the invention, a Fibroblast Growth Factor is present in the compositions at concentrations less than about 0.000006% w/w. In some embodiments of the invention, a Fibroblast Growth Factor is present in the compositions at concentrations less than about 0.000001% w/w. In some embodiments of the invention, more than one Fibroblast Growth Factor is present in the compositions of the present invention, each independently at concentrations of at least from about 0.000001% w/w to about 0.01% w/w. In some embodiments of the invention, more than one Fibroblast Growth Factor is present in the compositions of the present invention, each independently at concentrations of at least from about 0.000001% w/w to about 0.001% w/w. In some embodiments of the invention, more than one Fibroblast Growth Factor is present in the compositions of the present invention, each independently at concentrations of at least from about 0.000001% w/w to about 0.0001% w/w. In some embodiments of the invention, more than one Fibroblast Growth Factor is present in the compositions of the present invention, each independently at concentrations of at least about 0.000001% w/w. In some embodiments of the invention, more than one Fibroblast Growth Factor is present in the compositions of the present invention, each independently at concentrations of at least about 0.000005% w/w. In some embodiments of the invention, more than one Fibroblast Growth Factor is present in the compositions of the present invention, each independently at concentrations of at least about 0.00001% w/w. In some embodiments of the invention, more than one Fibroblast Growth Factor is present in the compositions of the present invention, each independently at concentrations of at least about 0.00005% w/w. In some embodiments of the invention, more than one Fibroblast Growth Factor is present in the compositions of the present invention, each independently at concentrations of at least about 0.00006% w/w. In some embodiments of the invention, more than one Fibroblast Growth Factor is present in the compositions of the present invention, each independently at concentrations of at least about 0.0001% w/w. In some embodiments of the invention, more than one Fibroblast Growth Factor is present in the compositions of the present invention, each independently at concentrations of at least about 0.00015% w/w. In some embodiments of the invention, more than one Fibroblast Growth Factor is present in the compositions, each independently at concentrations less than about 0.01% w/w. In some embodiments of the invention, more than one Fibroblast Growth Factor is present in the compositions, each independently at concentrations less than about 0.007% w/w. In some embodiments of the invention, more than one Fibroblast Growth Factor is present in the compositions, each independently at concentrations less than about 0.006% w/w. In some embodiments of the invention, more than one Fibroblast Growth Factor is present in the compositions, each independently at concentrations less than about 0.001% w/w. In some embodiments of the invention, more than one Fibroblast Growth Factor is present in the compositions, each independently at concentrations less than about 0.0007% w/w. In some embodiments of the invention, more than one Fibroblast Growth Factor is present in the compositions, each independently at concentrations less than about 0.0006% w/w. In some embodiments of the invention, more than one Fibroblast Growth Factor is present in the compositions, each independently at concentrations less than about 0.00010% w/w. In some embodiments of the invention, more than one Fibroblast Growth Factor is present in the compositions, each independently at concentrations less than about 0.000065% w/w. In some embodiments of the invention, more than one Fibroblast Growth Factor is present in the compositions, each independently at concentrations less than about 0.000001% w/w.

In some embodiments, Keratinocyte Growth Factor-1 is present in the compositions of the present invention at concentrations of at least from about 0.000001% w/w to about 0.01% w/w. In some embodiments, Keratinocyte Growth Factor-1 is present in the compositions of the present invention at concentrations of at least from about 0.000001% w/w to about 0.001% w/w. In some embodiments, Keratinocyte Growth Factor-1 is present in the compositions of the present invention at concentrations of at least from about 0.000001% w/w to about 0.0001% w/w. In some embodiments, Keratinocyte Growth Factor-1 is present in the compositions of the present invention at concentrations of at least about 0.000001% w/w. In some embodiments, Keratinocyte Growth Factor-1 is present in the compositions of the present invention at concentrations of at least about 0.000006% w/w. In some embodiments, Keratinocyte Growth Factor-1 is present in the compositions of the present invention at concentrations of at least about 0.00001% w/w. In some embodiments, Keratinocyte Growth Factor-1 is present in the compositions of the present invention at concentrations of at least about 0.00005%; w/w. In some embodiments, Keratinocyte Growth Factor-1 is present in the compositions of the present invention at concentrations of at least about 0.00006% w/w. In some embodiments, Keratinocyte Growth Factor-1 is present in the compositions of the present invention at concentrations of at least about 0.0001% w/w. In some embodiments, Keratinocyte Growth Factor-1 is present in the compositions of the present invention at concentrations of at least about 0.0006% w/w. In some embodiments, Keratinocyte Growth Factor-1 is present in the compositions of the present invention at concentrations of at least about 0.001% w/w. In other embodiments, Keratinocyte Growth Factor-1 is present in the compositions at concentrations less than about 0.01% w/w. In other embodiments, Keratinocyte Growth Factor-1 is present in the compositions at concentrations less than about 0.006% w/w. In other embodiments, Keratinocyte Growth Factor-1 is present in the compositions at concentrations less than about 0.001% w/w. In other embodiments, Keratinocyte Growth Factor-1 is present in the compositions at concentrations less than about 0.0007% w/w. In other embodiments, Keratinocyte Growth Factor-1 is present in the compositions at concentrations less than about 0.0006% w/w. In other embodiments, Keratinocyte Growth Factor-1 is present in the compositions at concentrations less than about 0.00010% w/w. In other embodiments, Keratinocyte Growth Factor-1 is present in the compositions at concentrations less than about 0.00007% w/w. In other embodiments, Keratinocyte Growth Factor-1 is present in the compositions at concentrations less than about 0.00006% w/w. In other embodiments, Keratinocyte Growth Factor-1 is present in the compositions at concentrations less than about 0.00001% w/w. In other embodiments, Keratinocyte Growth Factor-1 is present in the compositions at concentrations less than about 0.000006% w/w.

In some embodiments, Keratinocyte Growth Factor-2 is present in the compositions of the present invention at concentrations of at least from about 0.000001% w/w to about 0.01% w/w. In some embodiments, Keratinocyte Growth Factor-2 is present in the compositions of the present invention at concentrations of at least from about 0.000001% w/w to about 0.001% w/w. In some embodiments, Keratinocyte Growth Factor-2 is present in the compositions of the present invention at concentrations of at least from about 0.000001% w/w to about 0.0001% w/w. In other embodiments, Keratinocyte Growth Factor-2 is present in the compositions of the present invention at concentrations of at least about 0.000001% w/w. In other embodiments, Keratinocyte Growth Factor-2 is present in the compositions of the present invention at concentrations of at least about 0.000006% w/w. In other embodiments, Keratinocyte Growth Factor-2 is present in the compositions of the present invention at concentrations of at least about 0.00001% w/w. In other embodiments, Keratinocyte Growth Factor-2 is present in the compositions of the present invention at concentrations of at least about 0.00005% w/w. In other embodiments, Keratinocyte Growth Factor-2 is present in the compositions of the present invention at concentrations of at least about 0.00006% w/w. In other embodiments, Keratinocyte Growth Factor-2 is present in the compositions of the present invention at concentrations of at least about 0.0001% w/w. In other embodiments, Keratinocyte Growth Factor-2 is present in the compositions of the present invention at concentrations of at least about 0.0005% w/w. In other embodiments, Keratinocyte Growth Factor-2 is present in the compositions of the present invention at concentrations of at least about 0.001% w/w. In yet other embodiments, Keratinocyte Growth Factor-2 is present in the compositions at concentrations less than about 0.01% w/w. In yet other embodiments, Keratinocyte Growth Factor-2 is present in the compositions at concentrations less than about 0.006% w/w. In yet other embodiments, Keratinocyte Growth Factor-2 is present in the compositions at concentrations less than about 0.001% w/w. In yet other embodiments, Keratinocyte Growth Factor-2 is present in the compositions at concentrations less than about 0.0007% w/w. In yet other embodiments, Keratinocyte Growth Factor-2 is present in the compositions at concentrations less than about 0.0006% w/w. In yet other embodiments, Keratinocyte Growth Factor-2 is present in the compositions at concentrations less than about 0.00010% w/w. In yet other embodiments, Keratinocyte Growth Factor-2 is present in the compositions at concentrations less than about 0.00007% w/w. In yet other embodiments, Keratinocyte Growth Factor-2 is present in the compositions at concentrations less than about 0.00006% w/w. In yet other embodiments, Keratinocyte Growth Factor-2 is present in the compositions at concentrations less than about 0.00001% w/w. In yet other embodiments, Keratinocyte Growth Factor-2 is present in the compositions at concentrations less than about 0.000007% w/w. In yet other embodiments, Keratinocyte Growth Factor-2 is present in the compositions at concentrations less than about 0.000001% w/w.

In some embodiments, Transforming Growth Factor-$\beta$1 is present in compositions of the present invention at concentrations of at least from about 0.000001% w/w to about 0.001% w/w. In some embodiments, Transforming Growth Factor-$\beta$1 is present in compositions of the present invention at concentrations of at least from about 0.000001% w/w to about 0.0005% w/w. In some embodiments, Transforming Growth Factor-$\beta$1 is present in compositions of the present invention at concentrations of at least from about 0.000001% w/w to about 0.0001% w/w. In some embodiments, Transforming Growth Factor-$\beta$1 is present in compositions of the present invention at concentrations of at least from about 0.000001% w/w to about 0.0001% w/w. In some embodiments, Transforming Growth Factor-$\beta$1 is present in compositions of the present invention at concentrations of at least about 0.000001% w/w. In some embodiments, Transforming Growth Factor-$\beta$1 is present in compositions of the present invention at concentrations of at least about 0.000005% w/w. In some embodiments, Transforming Growth Factor-$\beta$1 is present in compositions of the present invention at concentrations of at least about 0.00001% w/w. In some embodiments, Transforming Growth Factor-$\beta$1 is present in compositions of the present invention at concentrations of at least about 0.000015% w/w. In some embodiments, Transforming Growth Factor-$\beta$1 is present in compositions of the present invention at concentrations of at least about 0.00002% w/w. In some embodiments, Transforming Growth Factor-$\beta$1 is present in compositions of the present invention at concentrations of at least about 0.00007% w/w. In some embodiments, Transforming Growth Factor-$\beta$1 is present in compositions of the present invention at concentrations of at least about 0.0002% w/w. In some embodiments, Transforming Growth Factor-$\beta$1 is present in compositions of the present invention at concentrations of at least about 0.0007% w/w. In some embodiments, Transforming Growth Factor-$\beta$1 is present in compositions of the present invention at concentrations of less than about 0.001% w/w. In some embodiments, Transforming Growth Factor-$\beta$1 is present in compositions of the present invention at concentrations of less than about 0.00075% w/w. In some embodiments, Transforming Growth Factor-$\beta$1 is present in compositions of the present invention at concentrations of less than about 0.00025% w/w. In some embodiments, Transforming Growth Factor-$\beta$1 is present in compositions of the present invention at concentrations of less than about 0.0002% w/w. In some embodiments, Transforming Growth Factor-$\beta$1 is present in compositions of the present invention at concentrations of less than about 0.000075% w/w. In some embodiments, Transforming Growth Factor-$\beta$1 is present in compositions of the present invention at concentrations of less than about 0.000025% w/w. In some embodiments, Transforming Growth Factor-$\beta$1 is present in compositions of the present invention at concentrations of less than about 0.00002% w/w. In some embodiments, Transforming Growth Factor-$\beta$1 is present in compositions of the present invention at concentrations of less than about 0.00001% w/w.

In some embodiments, a myristoylated peptide is present in the compositions of the invention at concentrations of at least from about 0.001% w/w to about 2.0% w/w. In some embodiments, a myristoylated peptide is present in the compositions of the invention at concentrations of at least from about 0.01% w/w to about 2.0% w/w. In some embodiments, a myristoylated peptide is present in the compositions of the invention at concentrations of at least from about 0.05% w/w to about 2.0% w/w. In some embodiments, a myristoylated peptide is present in the compositions of the invention at concentrations of at least from about 0.01% w/w to about 2.0% w/w. In some embodiments, a myristoylated peptide is present in the compositions of the invention at concentrations of at least about 0.001% w/w. In some embodiments, a myristoylated peptide is present in the compositions of the invention at concentrations of at least about 0.005% w/w. In some embodiments, a myristoylated peptide is present in the compositions of the invention at concentrations of at least about 0.01% w/w. In some embodiments, a myristoylated peptide is present in the compositions of the invention at concentrations of at least about 0.04% w/w. In some embodiments, a myristoylated peptide is present in the compositions of the invention at concentrations of at least about 0.05% w/w. In some embodiments, a myristoylated peptide is present in the compositions of the invention at concentrations of at least about 0.10% w/w. In some embodiments, a myristoylated peptide is present in the compositions of the invention at concentrations of at least about 0.40% w/w. In some embodiments, a myristoylated peptide is present in the compositions of the invention at concentrations of at least about 0.50% w/w. In some embodiments, a myristoylated peptide is present in the compositions of the invention at concentrations of at least about 1.00% w/w. In some embodiments, a myristoylated peptide is present in the compositions of the invention at concentrations of at least about 1.40% w/w. In some embodiments, a myristoylated peptide is present in the compositions of the invention at concentrations of at least about 1.50% w/w. In some embodiments, a myristoylated peptide is present in the compositions of the invention at concentrations of at least about 2.00% w/w. In some embodiments, a myristoylated peptide is present in the compositions of the invention at concentrations less than about 2.00% w/w. In some embodiments, a myristoylated peptide is present in the compositions of the invention at concentrations less than about 1.50% w/w. In some embodiments, a myristoylated peptide is present in the compositions of the invention at concentrations less than about 1.00% w/w. In some embodiments, a myristoylated peptide is present in the compositions of the invention at concentrations less than about 0.75% w/w. In some embodiments, a myristoylated peptide is present in the compositions of the invention at concentrations less than about 0.50% w/w. In some embodiments, a myristoylated peptide is present in the compositions of the invention at concentrations less than about 0.10% w/w. In some embodiments, a myristoylated peptide is present in the compositions of the invention at concentrations less than about 0.05% w/w. In some embodiments, a myristoylated peptide is present in the compositions of the invention at concentrations less than about 0.001% w/w. In some embodiments, a myristoylated peptide is present in the compositions of the invention at concentrations less than about 0.0005% w/w. In some embodiments, a myristoylated peptide is present in the compositions of the invention at concentrations less than about 0.0001% w/w. In some embodiments, more than one myristoylated peptide is present in the compositions of the inventions, each independently at concentrations of at least from about 0.001% w/w to about 2.0% w/w. In some embodiments, more than one myristoylated peptide is present in the compositions of the inventions, each independently at concentrations of at least from about 0.01% w/w to about 2.0% w/w. In some embodiments, more than one myristoylated peptide is present in the compositions of the inventions, each independently at concentrations of at least from about 0.05% w/w to about 2.0% w/w. In some embodiments, more than one myristoylated peptide is present in the compositions of the inventions, each independently at concentrations of at least from about 0.01% w/w to about 2.0% w/w. In some embodiments, more than one myristoylated peptide is present in the compositions of the invention, each independently at concentrations of at least about 0.001% w/w. In some embodiments, more than one myristoylated peptide is present in the compositions of the invention, each independently at concentrations of at least about 0.005% w/w. In some embodiments, more than one myristoylated peptide is present in the compositions of the invention, each independently at concentrations of at least about 0.01% w/w. In some embodiments, more than one myristoylated peptide is present in the compositions of the invention, each independently at concentrations of at least about 0.04% w/w. In some embodiments, more than one myristoylated peptide is present in the compositions of the invention, each independently at concentrations of at least about 0.05% w/w. In some embodiments, more than one myristoylated peptide is present in the compositions of the invention, each independently at concentrations of at least about 0.10% w/w. In some embodiments, more than one myristoylated peptide is present in the compositions of the invention, each independently at concentrations of at least about 0.20% w/w. In some embodiments, more than one myristoylated peptide is present in the compositions of the invention, each independently at concentrations of at least about 0.40% w/w In some embodiments, more than one myristoylated peptide is present in the compositions of the invention, each independently at concentrations of at least about 0.50% w/w. In some embodiments, more than one myristoylated peptide is present in the compositions of the invention, each independently at concentrations of at least about 1.00% w/w. In some embodiments, more than one myristoylated peptide is present in the compositions of the invention, each independently at concentrations of at least about 1.50% w/w. In some embodiments, more than one myristoylated peptide is present in the compositions of the invention, each independently at concentrations of at least about 2.00% w/w. In some embodiments, more than one myristoylated peptide may be present in the compositions of the invention, each independently at concentrations less than about 2.00% w/w. In some embodiments, more than one myristoylated peptide may be present in the compositions of the invention, each independently at concentrations less than about 1.50% w/w. In some embodiments, more than one myristoylated peptide may be present in the compositions of the invention, each independently at concentrations less than about 1.00% w/w. In some embodiments, more than one myristoylated peptide may be present in the compositions of the invention, each independently at concentrations less than about 0.60% w/w. In some embodiments, more than one myristoylated peptide may be present in the compositions of the invention, each independently at concentrations less than about 0.50% w/w. In some embodiments, more than one myristoylated peptide may be present in the compositions of the invention, each independently at concentrations less than about 0.10% w/w. In some embodiments, more than one myristoylated peptide may be present in the compositions of the invention, each independently at concentrations less than about 0.05% w/w. In some embodiments, more than one myristoylated peptide may be present in the compositions of the invention, each independently at concentrations less than about 0.001% w/w. In some embodiments, more than one myristoylated peptide may be present in the compositions of the invention, each independently at concentrations less than about 0.0001% w/w.

In some embodiments, a palmitoylated peptide is present in the compositions of the present invention at concentrations of at least from about 0.50% w/w to about 6.00% w/w. In some embodiments, a palmitoylated peptide is present in the compositions of the invention at concentrations of at least about 0.50% w/w. In some embodiments, a palmitoylated peptide is present in the compositions of the invention at concentrations of at least about 1.00% w/w. In some embodiments, a palmitoylated peptide is present in the compositions of the invention at concentrations of at least about 1.50% w/w. In some embodiments, a palmitoylated peptide is present in the compositions of the invention at concentrations of at least about 2.00% w/w. In some embodiments, a palmitoylated peptide is present in the compositions of the invention at concentrations of at least about 2.50% w/w. In some embodiments, a palmitoylated peptide is present in the compositions of the invention at concentrations of at least about 3.00% w/w. In some embodiments, a palmitoylated peptide is present in the compositions of the invention at concentrations of at least about 3.50% w/w. In some embodiments, a palmitoylated peptide is present in the compositions of the invention at concentrations of at least about 4.00% w/w In some embodiments, a palmitoylated peptide is present in the compositions of the invention at concentrations of at least about 4.50% w/w. In some embodiments, a palmitoylated peptide is present in the compositions of the invention at concentrations of at least about 5.00% w/w. In some embodiments, a palmitoylated peptide is present in the compositions of the invention at concentrations of at least about 5.50% w/w. In some embodiments, a palmitoylated peptide is present in the compositions of the invention at concentrations of at least about 6.00% w/w. In some embodiments, a palmitoylated peptide is present in the compositions of the invention at concentrations of less than about 6.00% w/w. In some embodiments, a palmitoylated peptide is present in the compositions of the invention at concentrations of less than about 5.50% w/w. In some embodiments, a palmitoylated peptide is present in the compositions of the invention at concentrations of less than about 5.00% w/w. In some embodiments, a palmitoylated peptide is present in the compositions of the invention at concentrations of less than about 4.50% w/w. In some embodiments, a palmitoylated peptide is present in the compositions of the invention at concentrations of less than about 4.00% w/w. In some embodiments, a palmitoylated peptide is present in the compositions of the invention at concentrations of less than about 3.50% w/w. In some embodiments, a palmitoylated peptide is present in the compositions of the invention at concentrations of less than about 3.00% w/w. In some embodiments, a palmitoylated peptide is present in the compositions of the invention at concentrations of less than about 2.50% w/w. In some embodiments, a palmitoylated peptide is present in the compositions of the invention at concentrations of less than about 2.00% w/w. In some embodiments, a palmitoylated peptide is present in the compositions of the invention at concentrations of less than about 1.50% w/w. In some embodiments, a palmitoylated peptide is present in the compositions of the invention at concentrations of less than about 1.00% w/w. In some embodiments, a palmitoylated peptide is present in the compositions of the invention at concentrations of less than about 0.50% w/w. In some embodiments, more than one palmitoylated peptide is present in the compositions of the invention each independently at concentrations of at least about 0.50% w/w. In some embodiments, more than one palmitoylated peptide is present in the compositions of the invention each independently at concentrations of at least about 1.00% w/w. In some embodiments, more than one palmitoylated peptide is present in the compositions of the invention each independently at concentrations of at least about 1.50% w/w. In some embodiments, more than one palmitoylated peptide is present in the compositions of the invention each independently at concentrations of at least about 2.00% w/w. In some embodiments, more than one palmitoylated peptide is present in the compositions of the invention each independently at concentrations of at least about 2.50% w/w. In some embodiments, more than one palmitoylated peptide is present in the compositions of the invention each independently at concentrations of at least about 3.00% w/w. In some embodiments, more than one palmitoylated peptide is present in the compositions of the invention each independently at concentrations of at least about 3.50% w/w. In some embodiments, more than one palmitoylated peptide is present in the compositions of the invention each independently at concentrations of at least about 4.00% w/w. In some embodiments, more than one palmitoylated peptide is present in the compositions of the invention each independently at concentrations of at least about 4.50% w/w. In some embodiments, more than one palmitoylated peptide is present in the compositions of the invention each independently at concentrations of at least about 5.00% w/w. In some embodiments, more than one palmitoylated peptide is present in the compositions of the invention each independently at concentrations of at least about 5.50% w/w. In some embodiments, more than one palmitoylated peptide is present in the compositions of the invention each independently at concentrations of at least about 6.00% w/w. In some embodiments, more than one palmitoylated peptide is present in the compositions of the invention, each independently at concentrations of less than about 6.00% w/w. In some embodiments, more than one palmitoylated peptide is present in the compositions of the invention, each independently at concentrations of less than about 5.50% w/w. In some embodiments, more than one palmitoylated peptide is present in the compositions of the invention, each independently at concentrations of less than about 5.00% w/w. In some embodiments, more than one palmitoylated peptide is present in the compositions of the invention, each independently at concentrations of less than about 4.50% w/w. In some embodiments, more than one palmitoylated peptide is present in the compositions of the invention, each independently at concentrations of less than about 4.00% w/w. In some embodiments, more than one palmitoylated peptide is present in the compositions of the invention, each independently at concentrations of less than about 3.50% w/w. In some embodiments, more than one palmitoylated peptide is present in the compositions of the invention, each independently at concentrations of less than about 3.00% w/w. 2. In some embodiments, more than one palmitoylated peptide is present in the compositions of the invention, each independently at concentrations of less than about 2.50% w/w. In some embodiments, more than one palmitoylated peptide is present in the compositions of the invention, each independently at concentrations of less than about 2.00% w/w. In some embodiments, more than one palmitoylated peptide is present in the compositions of the invention, each independently at concentrations of less than about 1.50% w/w. In some embodiments, more than one palmitoylated peptide is present in the compositions of the invention, each independently at concentrations of less than about 1.00% w/w. In some embodiments, more than one palmitoylated peptide is present in the compositions of the invention, each independently at concentrations of less than about 0.50% w/w.

In some embodiments, one or more antioxidants are present in the compositions of the invention, each independently at concentrations present in the compositions of the invention at concentrations of at least from about 0.001% w/w to about 2.0% w/w. In some embodiments, one or more antioxidants are present in the compositions of the invention, each independently at concentrations present in the compositions of the invention at concentrations of at least from about 0.01% w/w to about 2.0% w/w. In some embodiments, one or more antioxidants are present in the compositions of the invention, each independently at concentrations present in the compositions of the invention at concentrations of at least from about 0.05% w/w to about 2.0% w/w. In some embodiments, one or more antioxidants are present in the compositions of the invention, each independently at concentrations present in the compositions of the invention at concentrations of at least from about 0.01% w/w to about 2.0% w/w. In some embodiments, one or more antioxidants are present in the compositions of the invention, each independently at concentrations of at least about 0.001% w/w. In some embodiments, one or more antioxidants are present in the compositions of the invention, each independently at concentrations of at least about 0.005% w/w. In some embodiments, one or more antioxidants are present in the compositions of the invention, each independently at concentrations of at least about 0.01% w/w. In some embodiments, one or more antioxidants are present in the compositions of the invention, each independently at concentrations of at least about 0.05% w/w. In some embodiments, one or more antioxidants are present in the compositions of the invention, each independently at concentrations of at least about 0.10% w/w. In some embodiments, one or more antioxidants are present in the compositions of the invention, each independently at concentrations of at least about 0.50% w/w. In some embodiments, one or more antioxidants are present in the compositions of the invention, each independently at concentrations of at least about 1.00% w/w. In some embodiments, one or more antioxidants are present in the compositions of the invention, each independently at concentrations of at least about 1.50% w/w. In some embodiments, one or more antioxidants are present in the compositions of the invention, each independently at concentrations of at least about 2.00% w/w. In some embodiments, one or more antioxidants are present in the compositions of the invention, each independently at concentrations less than about 2.00% w/w. In some embodiments, one or more antioxidants are present in the compositions of the invention, each independently at concentrations less than about 1.50% w/w. In some embodiments, one or more antioxidants are present in the compositions of the invention, each independently at concentrations less than about 1.00% w/w. In some embodiments, one or more antioxidants are present in the compositions of the invention, each independently at concentrations less than about 0.50% w/w. In some embodiments, one or more antioxidants are present in the compositions of the invention, each independently at concentrations less than about 0.10% w/w. In some embodiments, one or more antioxidants are present in the compositions of the invention, each independently at concentrations less than about 0.05% w/w. In some embodiments, one or more antioxidants are present in the compositions of the invention, each independently at concentrations less than about 0.001% w/w. In some embodiments, one or more antioxidants are present in the compositions of the invention, each independently at concentrations less than about 0.005% w/w. In some embodiments, one or more antioxidants are present in the compositions of the invention, each independently at concentrations less than about 0.0001% w/w.

In some embodiments, ubiquinone is present in the compositions of the invention at concentrations present in the compositions of the invention at concentrations of at least from about 0.001% w/w to about 2.0% w/w. In some embodiments, ubiquinone is present in the compositions of the invention at concentrations present in the compositions of the invention at concentrations of at least from about 0.01% w/w to about 2.0% w/w. In some embodiments, ubiquinone is present in the compositions of the invention at concentrations present in the compositions of the invention at concentrations of at least from about 0.05% w/w to about 2.0% w/w. In some embodiments, ubiquinone is present in the compositions of the invention at concentrations present in the compositions of the invention at concentrations of at least from about 0.01% w/w to about 2.0% w/w. In some embodiments, ubiquinone is present in the compositions of the invention, at concentrations of at least about 0.001% w/w. In some embodiments, ubiquinone is present in the compositions of the invention, at concentrations of at least about 0.005% w/w. In some embodiments, ubiquinone is present in the compositions of the invention, at concentrations of at least about 0.01% w/w. In some embodiments, ubiquinone is present in the compositions of the invention, at concentrations of at least about 0.05% w/w. In some embodiments, ubiquinone is present in the compositions of the invention, at concentrations of at least about 0.10% w/w. In some embodiments, ubiquinone is present in the compositions of the invention, at concentrations of at least about 0.20% w/w. In some embodiments, ubiquinone is present in the compositions of the invention, at concentrations of at least about 0.30% w/w. In some embodiments, ubiquinone is present in the compositions of the invention, at concentrations of at least about 0.40% w/w. In some embodiments, ubiquinone is present in the compositions of the invention, at concentrations of at least about 0.50% w/w. In some embodiments, ubiquinone is present in the compositions of the invention, at concentrations of at least about 0.60% w/w. In some embodiments, ubiquinone is present in the compositions of the invention, at concentrations of at least about 0.70% w/w. In some embodiments, ubiquinone is present in the compositions of the invention, at concentrations of at least about 0.80% w/w. In some embodiments, ubiquinone is present in the compositions of the invention, at concentrations of at least about 1.00% w/w. In some embodiments, ubiquinone is present in the compositions of the invention, at concentrations of at least about 1.50% w/w. In some embodiments, ubiquinone is present in the compositions of the invention, at concentrations of at least about 2.00% w/w. In some embodiments, ubiquinone is present in the compositions of the invention at concentrations less than about 2.00% w/w. In some embodiments, ubiquinone is present in the compositions of the invention at concentrations less than about 1.50% w/w. In some embodiments, ubiquinone is present in the compositions of the invention at concentrations less than about 1.00% w/w. In some embodiments, ubiquinone is present in the compositions of the invention at concentrations less than about 0.60% w/w. In some embodiments, ubiquinone is present in the compositions of the invention at concentrations less than about 0.50% w/w. In some embodiments, ubiquinone is present in the compositions of the invention at concentrations less than about 0.40% w/w. In some embodiments, ubiquinone is present in the compositions of the invention at concentrations less than about 0.30% w/w. In some embodiments, ubiquinone is present in the compositions of the invention at concentrations less than about 0.20% w/w. In some embodiments, ubiquinone is present in the compositions of the invention at concentrations less than about 0.10% w/w. In some embodiments, ubiquinone is present in the compositions of the invention at concentrations less than about 0.05% w/w. In some embodiments, ubiquinone is present in the compositions of the invention at concentrations less than about 0.001% w/w. In some embodiments, ubiquinone is present in the compositions of the invention at concentrations less than about 0.005% w/w. In some embodiments, ubiquinone is present in the compositions of the invention at concentrations less than about 0.0001% w/w.

In some embodiments, green tea extract is present in the compositions of the invention at concentrations present in the compositions of the invention at concentrations of at least from about 0.001% w/w to about 2.0% w/w. In some embodiments, green tea extract is present in the compositions of the invention at concentrations present in the compositions of the invention at concentrations of at least from about 0.01% w/w to about 2.0% w/w. In some embodiments, green tea extract is present in the compositions of the invention at concentrations present in the compositions of the invention at concentrations of at least from about 0.05% w/w to about 2.0% w/w. In some embodiments, green tea extract is present in the compositions of the invention at concentrations present in the compositions of the invention at concentrations of at least from about 0.01% w/w to about 2.0% w/w. In some embodiments, green tea extract is present in the compositions of the invention, at concentrations of at least about 0.001% w/w. In some embodiments, green tea extract is present in the compositions of the invention, at concentrations of at least about 0.005% w/w. In some embodiments, green tea extract is present in the compositions of the invention, at concentrations of at least about 0.01% w/w. In some embodiments, green tea extract is present in the compositions of the invention, at concentrations of at least about 0.05% w/w. In some embodiments, green tea extract is present in the compositions of the invention, at concentrations of at least about 0.10% w/w. In some embodiments, green tea extract is present in the compositions of the invention, at concentrations of at least about 0.50% w/w. In some embodiments, green tea extract is present in the compositions of the invention, at concentrations of at least about 0.75% w/w. In some embodiments, green tea extract is present in the compositions of the invention, at concentrations of at least about 1.00% w/w. In some embodiments, green tea extract is present in the compositions of the invention, at concentrations of at least about 1.50% w/w. In some embodiments, green tea extract is present in the compositions of the invention, at concentrations of at least about 2.00% w/w. In some embodiments, green tea extract is present in the compositions of the invention at concentrations less than about 2.00% w/w. In some embodiments, green tea extract is present in the compositions of the invention at concentrations less than about 1.50% w/w. In some embodiments, green tea extract is present in the compositions of the invention at concentrations less than about 1.00% w/w. In some embodiments, green tea extract is present in the compositions of the invention at concentrations less than about 0.70% w/w. In some embodiments, green tea extract is present in the compositions of the invention at concentrations less than about 0.60% w/w. In some embodiments, green tea extract is present in the compositions of the invention at concentrations less than about 0.50% w/w. In some embodiments, green tea extract is present in the compositions of the invention at concentrations less than about 0.40% w/w. In some embodiments, green tea extract is present in the compositions of the invention at concentrations less than about 0.30% w/w. In some embodiments, green tea extract is present in the compositions of the invention at concentrations less than about 0.20% w/w. In some embodiments, green tea extract is present in the compositions of the invention at concentrations less than about 0.10% w/w. In some embodiments, green tea extract is present in the compositions of the invention at concentrations less than about 0.05% w/w. In some embodiments, green tea extract is present in the compositions of the invention at concentrations less than about 0.001% w/w. In some embodiments, green tea extract is present in the compositions of the invention at concentrations less than about 0.005% w/w. In some embodiments, green tea extract is present in the compositions of the invention at concentrations less than about 0.0001% w/w.

In some embodiments of the invention, the compositions described herein are applied topically to the skin of a human to reduce inflammation from either intrinsic or extrinsic sources. In other embodiments of the invention, the compositions described herein are applied topically to the skin of a human to reduce oxidative stress from either extrinsic or intrinsic sources. In other embodiments of the invention, the compositions described herein are applied topically to the skin of a human to produce a skin brightening effect. In other embodiments of the invention, the compositions described herein are applied topically to the skin of a human to reduce fine lines and wrinkles in skin. In some other embodiments of the invention, the compositions described herein are applied topically to the skin of a human to enhance elasticity of skin. In other embodiments of the invention, the compositions described herein are applied topically to the skin of a human to reduce the appearance of scarring and lesions of the skin due to extrinsic and intrinsic factors

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

I. Skin Care Compositions

Compositions of the present invention are useful in helping to reduce the appearance of the signs of biological or environmentally-caused aging, including fine lines, wrinkles, age spots and reduced skin elasticity. In one aspect of the present invention relates to topically-applied cosmetic or dermatological compositions comprising (i) telomerase; (ii) a myristoylated peptide; and (iii) two specific growth factors (an Epidermal Growth Factor and a Keratinocyte Growth Factor) Biological aging, also known as intrinsic aging or senescence, is manifested as fine lines, wrinkles and deepening of facial expression lines. Intrinsically-aged skin is thin and inelastic. Photodamage and other extrinsic causes of skin aging can be manifested in skin that appears yellowed, blemished, mottled (i.e., in terms of pigmentation), coarsely wrinkled and furrowed. Extrinsically-aged skin can appear thickened, lax, rough and leathery. There has been and remains a need for cosmeceutical products that better address both intrinsic and extrinsic causes of skin aging. The compositions of the present invention may be used to slow or prevent symptoms of aging skin.

At a physiological level, intrinsically-aged skin has changes in skin matrix proteins, including collagen and elastin. Senescent skin fibroblasts produce lesser amounts of these proteins. Additionally, aged skin is characterized by increased levels of enzymes, such as collagenase and matrix metalloproteinase (MMPs) that break down the skin matrix. At a cellular level, the increased production of collagenase and MMPs and concomitant decrease in the rate of synthesis of collagen and elastin is a result of an altered pattern of gene expression. More particularly, expression of genes that code for enzymes that break down the skin matrix is increased, while expression of genes that code for the synthesis of the matrix proteins themselves is decreased.

A. Skin Care Actives

In the compositions and methods described herein, a number of skin care actives are included.

Telomerase.

At a chromosomal level, the altered pattern of gene expression in the senescent process is due in part to the activity of telomeres. Telomeres are structures on ends of chromosomes consisting of repetitive segments of DNA that regulate the replication of the chromosomes and thus regulate the process of cellular division. In humans, telomeres have the repetitive sequence TTAGGG. Some have described telomeres as "molecular switches" that initiate the sequence of chromosomal replication and duplication.

Each time a cell divides, telomeres shorten by a small amount. After repeated cell divisions, telomeres shortened past a critical threshold are unable to initiate chromosomal replication. Cell division thus ceases, causing the cell to become senescent. Recently an enzyme, telomerase, was identified and characterized which can "rebuild" telomeres, thus prolonging the viability of cells.

More specifically, telomerase comprises two distinct component molecules. The first component, designated TR, is Telomerase RNA. The second protein component of telomerase is Telomerase Reverse Transcriptase (TRT), which reads the component RNA template (TR) to build the complementary DNA strand and thus directs the synthesis of the repeated TTAGGG sequences that form the telomere. It is in this manner that telomerase lengthens telomeres. The respective components of the human form are human Telomerase RNA (hTR) and human Telomerase Reverse Transcriptase (hTRT). These components, singly and in combination, are useful skin care actives.

In one embodiment of the invention, the component of telomerase incorporated in the compositions of the invention has an amino acid sequence with at least 90%, 95%, 98%, or 99% sequence homology to the amino acid sequence of a telomerase reverse transcriptase of an animal. In another embodiment of the invention, the component of telomerase incorporated in the compositions of the invention has an amino acid sequence with at least 90%, 95%, 98%, or 99% sequence homology to the amino acid sequence of a telomerase RNA of any animal. In another embodiment of the present invention the component of telomerase incorporated in the compositions of the invention has an amino acid sequence with at least 90%, 95%, 98%, or 99% sequence homology to the amino acid sequence of human telomerase RNA (hTR). In yet another embodiment of the present invention, the component of telomerase incorporated in the compositions of the invention has an amino acid sequence with at least 90%, 95%, 98%, or 99% sequence homology to the amino acid sequence of a human telomerase reverse transcriptase (hTRT). In some embodiments of the invention, the components of telomerase are produced via recombinant technology. These components of telomerase enzyme may be obtained upon purification by known methods from commercial cell lines transfected with cDNA expressing the component, for example, e.g., hTRT. One example of such a cDNA is available from CAMBIA.

Inhibitor of Telomerase.

In another embodiment of the invention, inhibition of inappropriate telomerase activity by an inhibitor of a component of telomerase may provide utility for inclusion as a skin active. In some embodiments of the invention, the inhibitor to a component of a telomerase is a small molecule, a peptide, a nucleic acid, an oligonucleotide, or a protein. In some embodiments of the invention, the inhibitor is an antibody to a component of telomerase. In some embodiments of the invention, the antibody has an amino acid sequence with at least 90%, 95%, 98%, or 99% sequence homology to the amino acid sequence of an antibody to animal telomerase. In other embodiments of the invention, the antibody has an amino acid sequence with at least 90%, 95%, 98%, or 99% sequence homology to the amino acid sequence of an antibody to a component of human telomerase. In some embodiments of the invention, the antibody is a human telomerase RT antibody. In some embodiments, the antibody is a human telomerase RNA antibody. An example of an antibody useful in skin care compositions is, for example, e.g., GTX30410 hTRT monoclonal antibody of human telomerase hTRT (clone 2C4), commercially available from GeneTex, Inc. (San Antonio, Tex.), which is specific for human TRT.

Growth Factors.

Growth factors, which are proteins capable of stimulating cellular proliferation and cellular differentiation, may be included as skin actives in the compositions of the invention. Growth factors are divided into classes including Epidermal Growth Factor (EGF), Transforming Growth Factor-β1 (TGF-β1), Vascular Endothelial Growth Factor (VEGF), Keratinocyte Growth Factors (KGF) and Fibroblast Growth Factor (FGF). Among the over twenty types of Fibroblast Growth Factors are Keratinocyte Growth Factors (KGF). These growth factors may be isolated from animal sources or made be made using recombinant technology.

Epidermal Growth Factor (EGF) has been shown to promote proliferation and differentiation of mesenchymal and epithelial cells. In-vitro, EGF promotes colony formation of epidermal cells in culture and in-vivo it promotes epithelial development. In some embodiments the EGF has the amino acid sequence of the EGF of an animal. In other embodiments the EGF has the amino acid sequence of the EGF of a human. An example is recombinant human EGF, commercially available form R&D Systems, which is an N-methionyl form of the 54 amino acid sequence of the natural mature human EGF, with a predicted molecular mass of about 6 kDa.

Transforming Growth Factor-β1 (TGF-β1) is one of a large and diverse family of growth factors, i.e., including the bone morphogenetic proteins. TGF-β1 has multiple cell-context specific effects but may have protective effects on keratinocytes. In some embodiments, the TGF-β1 has the amino acid sequence of the TGF-β1 of an animal. In other embodiments, the TGF-β1 has the sequence of the TGF-β1 of a human. An example of TGF-β1 is a disulfide linked homodimeric recombinant form of human TGF-β1 (SEQ ID NO. 5), which is available from R&D Systems, with a predicted molecular mass of about 25 kDa.

Vascular Endothelial Growth Factor (VEGF) has the ability to increase permeability of capillary vessels and promote angiogenesis. In some embodiments the VEGF has the amino acid sequence of the VEGF of an animal. In other embodiments, the VEGF has the amino acid sequence of the VEGF of a human. An example is a disulfide linked homodimeric human VEGF, which is available from R&D Systems and has a molecular mass of about 19-21 kDa.

The Fibroblast Growth Factor (FGF) family includes 22 known related cytokines which are involved in many functions including modulation of cell proliferation, differentiation, and migration. FGFs bind at tyrosine kinase receptors, and, in one aspect, are implicated in wound healing in complicated, interrelated modes. FGFs 1, 2, 5, 7, and 10 are upregulated during healing. The use of one or more of the 22 membered FGF family in the compositions of the invention may provide synergistic effects in stimulating new epidermal growth, thus providing improved skin conditioning.

The Keratinocyte Growth Factor subfamily of FGFs includes FGF-7 (also known as KGF-1) and KGF-2 (also known as FGF-10). These two growth factors are important in controlling epithelial cell behavior and can significantly promote re-epithelialization in both juvenile and mature animals. In one embodiment of the invention, the Keratinocyte Growth Factor is KGF-1. In another embodiment of the invention, the Keratinocyte Growth Factor is KGF-2. In another embodiment of the invention, the Keratinocyte Growth Factor is KGF-1. In some embodiments the KGF has the amino acid sequence of the KGF of an animal. In other embodiments, the KGF has the amino acid sequence of the KGF of a human.

In some embodiments of the invention, the composition contains an Epidermal Growth Factor and at least one Keratinocyte Growth Factor. In other embodiments, the composition contains an Epidermal Growth Factor, at least one Keratinocyte Growth Factor, and Transforming Growth Factor-β1. In yet other embodiments, the composition contains an Epidermal Growth Factor, at least one Keratinocyte Growth Factor, Transforming Growth Factor-β1, and a telomerase, which provides surprisingly efficacious use in topical treatment of skin. In yet other embodiments, the composition contains an Epidermal Growth Factor, at least one Keratinocyte Growth Factor, Transforming Growth Factor-β1, and an antibody to telomerase, which provides surprisingly efficacious use in topical treatment of skin.

Short Chain Peptides.

The use of short chain peptides, both with and without attached lipid moieties, in skincare products, is known to those of skill in the art. For example, Olay Regenerist products, sold by Procter & Gamble, contain, Matrixyl®, a palmitoylated pentapeptide having the sequence Pal-KTTKS. These additional skin care actives include peptides incorporating about two to about eleven amino acids.

N-Modified Peptides.

Compositions of the present invention include at least one myristoylated peptide. As used in the present invention, by the term myristoylated peptide is meant a peptide having a sequence of from about two to about eleven amino acids where a myristoyl group of the formula $CH_3(CH_2)_{12}COO-$ is attached to the N-terminus of the amino acid sequence.

In one embodiment, the compositions of the present invention comprise at least two acylated peptides having a sequence of from about two to about eleven amino acids, where at least one of the acylated peptides is myristoylated.

In another embodiment, the compositions of the present invention comprise at least two acylated peptides having a sequence of from about two to about eleven amino acids, at least two of which are myristoylated.

In yet another embodiment, the compositions of the present invention comprise at least two acylated peptides having a sequence of from about two to about eleven amino acids, at least one of which is myristoylated and one of which is palmitoylated. As used in the present invention, by the term palmitoylated peptide is meant a peptide having a sequence of from about two to about eleven amino acids where a palmitoyl group of the formula $CH_3(CH_2)_{14}COO-$ is attached to the N-terminus of the amino acid sequence.

Tri-, tetra-, penta-, hexa- and heptapeptides as well as oligopeptides (including palmitoyl and myristoyl derivatives thereof) suitable for incorporation in compositions of the present invention are commercially-available from a number of suppliers and are described in the *International Cosmetic Ingredient Dictionary and Handbook* (10th Edition, 2003) published by the Cosmetics Toiletries and Fragrance Association ("INCI Dictionary"). These include acylated peptides as described in U.S. Pat. Nos. 6,974,799 and 6,492,326. These peptides may comprise amino acid sequences which are homologous to portions of the sequences for Collagen 1.

In some embodiments of the invention, MYRISTOYL PENTAPEPTIDE-8 (MPP-GD), and MYRISTOYL PENTAPEPTIDE-11 (MPP-11), which are, for example, commercially available from Therapeutic Peptides, Inc. Harahan La., are incorporated in the skin care compositions. Another peptide, palmitoyl pentapeptide-4, also known as MATRIXYL™, having the sequence palmitoyl-Lys-Thr-Thr-Lys-Ser and commercially available from Personalformulator.com, Evanston, Wyo., may be incorporated in the compositions of the invention.

B. Skin Benefit Ingredients

Compositions of the present invention may contain an antioxidant, a humectant and/or a moisturizing agent. Other agents conferring a benefit may also include antifungals, antibacterials, and anti-inflammatory agents.

Antioxidants.

Antioxidants suitable for use in dermatological or cosmetic formulations are well-known to those of skill in the art. Non-limiting examples of antioxidants include the following: ascorbic acid and its salts, ascorbyl esters of fatty acids, ascorbic acid derivatives (e.g., magnesium ascorbyl phosphate, sodium ascorbyl phosphate, ascorbyl sorbate), tocopherol, tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters (e.g., propyl gallate), nordihydroguaiaretic acid, bioflavonoids, quinones, and ubiquinones including Coenzyme Q and its derivatives.

Antioxidants are useful in the compositions of the invention to reduce the effects of oxidative stress, brighten skin tone, and reduce hyperpigmentation, amongst their effects.

Ubiquinone.

Ubiquinone, also known as idebenone, is a quinone derivative. The use of idebenone can be used in treating aging of the skin, wrinkling of the skin, ultraviolet radiation-induced damage, as well as oxidative and "degenerative" processes, by applying topical compositions having an effective amount of idebenone or an idebenone derivative. Idenbenone or an idebenone derivative can be topically administered to reduce skin hyperpigmentation, skin irritation and/or inflammatory reactions in the skin. Idebenone may reduce the appearance of fine lines and wrinkles, as well as skin roughness and dryness and to even skin tone.

Coenzyme Q is a ubiquinone having isoprenoid side chains and may be expressed by the short-hand $CoQ_n$, where n is the number of isoprenoid units in the side chain. In one aspect of the present invention, n is an integer ranging from 0 to 12, preferably from 1 to 12, and more preferably from 6 to 10. In some embodiments, the Coenzyme Q, is Coenzyme $Q_{10}$.

Another aspect of the present invention relates to compositions comprising ubiquinones not having an isoprenoid side chain. These include alkyl-ubiquinones in which the alkyl group contains from 1 to 20, preferably from 1 to 12, carbon atoms. Non-limiting examples of such ubiquinones are decylubiquinones, 6-decylubiquinone, 2,3 dimethoxy-5-decyl-1,4-ubiquinone, as well as derivatives and mixtures thereof.

Another antioxidant useful in the compositions of the invention are polyphenolic bioflavonoids. In some embodiments of the invention, the composition comprises a green tea extract, which is an example of a polyphenolic bioflavonoid.

In some embodiments of the present invention, the composition comprises Coenzyme Q or a derivative thereof. In other embodiments, the composition comprises a bioflavonoid. In yet other embodiments, the composition comprises a polyphenol.

Other Antioxidants.

Other compounds with an antioxidant effect useful in the compositions of the invention alpha hydroxy acids (AHAs), poly-AHAs, complex poly-AHAs, retinoids, fish polysaccharides, anti-enzymatic agents, antioxidants such as ascorbic acid, pycnogenol, ursolic acid, vegetable isoflavones, vitamins A, C, and E, lipoic acid, resveratrol, 1-carnosine and taurine, agaricic acid, various plant extracts, and their derivatives. In some embodiments of the invention, one or more antioxidants are chosen from the group comprising retinyl palmitate, magnesium ascorbyl phosphate, sodium ascorbyl phosphate and tocopherol acetate.

Humectants.

Humectants suitable for use in dermatological or cosmetic formulations to assist in moisturizing skin are well-known to those of skill in the art and are taught in U.S. Pat. No. 6,492,326. Preferred, but non-limiting, examples of humectants and moisturizing agents include: sodium hyaluronate, D,L-panthenol, D-panthenol, methylsilanol mannuronate, natural oils (e.g., borage oil, evening primrose oil), $C_6$-$C_{22}$ fatty acid esters of glycerol, butylene glycol, silicones and silicone derivatives.

Other Anti-Inflammatory Agents.

Other anti-inflammatory agents which may be incorporated into the compositions of the invention include, but are not limited to mefenamic acid or derivatives thereof; phenylbutazone or derivatives thereof; indomethacin or derivatives thereof; ibuprofen or derivatives thereof; ketoprofen or derivatives thereof; ε-aminocapronic acid; sodium diclofenac; diphenhydramine; tranexamic acid or derivatives thereof; dexamethasone; cortisone or esters thereof; hydrocortisone or esters thereof; adrenal cortical hormone such as prednisone and prednisolone; and antihistamic agent.

Anti-Fungal and Anti-Microbial Agents.

Antimicrobial and antifungal agents may be incorporated into the compositions of the invention include but are not limited to beta-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate and clotrimazole.

II. Formulations

In some embodiments, Telomerase RNA is present in compositions of the present invention at concentrations of at least from about 0.000001% w/w to about 0.01% w/w; at least from about 0.000005% w/w to about 0.005% w/w; at least from about 0.00001% w/w to about 0.001% w/w; at least from about 0.00005% w/w to about 0.001% w/w, or at least from about 0.0001% w/w to about 0.001% w/w. In some embodiments, Telomerase RNA is present in compositions of the present invention at concentrations of more than about 0.000001%; 0.000002%; 0.000003%; 0.000004%; 0.000005%; 0.000006%; 0.000007%; 0.000008%; 0.000009%; 0.00001%; 0.00002%; 0.00003%; 0.00004%; 0.00005%; 0.00006%; 0.00007%; 0.00008%; 0.00009%; 0.0001%; 0.0002%; 0.0003%; 0.0004%; 0.0005%; 0.0006%; 0.0007%; 0.0008%; 0.0009%; 0.001%; 0.002%; 0.003%; 0.004%; 0.005%; 0.006%; 0.007%; 0.008%; 0.009%, or 0.01% w/w. In some embodiments, Telomerase RNA is present in compositions of the present invention at concentrations of less than about 0.01%; 0.009%; 0.008%; 0.007%; 0.006%; 0.005%; 0.004%; 0.003%; 0.002%; 0.001%; 0.0009%; 0.0008%; 0.0007%; 0.0006%; 0.0005%; 0.0004%; 0.0003%; 0.0002%; 0.0001%; 0.00009%; 0.00008%; 0.00007%; 0.00006%; 0.00005%; 0.00004%; 0.00003%; 0.00002%; 0.00001%; 0.000009%; 0.000008%; 0.000007%; 0.000006%; 0.000005%; 0.000004%; 0.000003%; 0.000002%; or 0.000001% w/w.

In some embodiments, Telomerase RT is present in compositions of the present invention at concentrations of at least from about 0.000001% w/w to about 0.01% w/w; at least from about 0.000005% w/w to about 0.005% w/w; at least from about 0.00001% w/w to about 0.001% w/w; at least from about 0.00005% w/w to about 0.001% w/w, or at least from about 0.0001% w/w to about 0.001% w/w. In some embodiments, Telomerase RT is present in compositions of the present invention at concentrations of more than about 0.000001%; 0.000002%; 0.000003%; 0.000004%; 0.000005%; 0.000006%; 0.000007%; 0.000008%; 0.000009%; 0.00001%; 0.00002%; 0.00003%; 0.00004%; 0.00005%; 0.00006%; 0.00007%; 0.00008%; 0.00009%; 0.0001%; 0.0002%; 0.0003%; 0.0004%; 0.0005%; 0.0006%; 0.0007%; 0.0008%; 0.0009%; 0.001%; 0.002%; 0.003%; 0.004%; 0.005%; 0.006%; 0.007%; 0.008%; 0.009%, or 0.01% w/w. In some embodiments, Telomerase RT is present in compositions of the present invention at concentrations of less than about 0.01%; 0.009%; 0.008%; 0.007%; 0.006%; 0.005%; 0.004%; 0.003%; 0.002%; 0.001%; 0.0009%; 0.0008%; 0.0007%; 0.0006%; 0.0005%; 0.0004%; 0.0003%; 0.0002%; 0.0001%; 0.00009%; 0.00008%; 0.00007%; 0.00006%; 0.00005%; 0.00004%; 0.00003%; 0.00002%; 0.00001%; 0.000009%; 0.000008%; 0.000007%; 0.000006%; 0.000005%; 0.000004%; 0.000003%; 0.000002%; or 0.000001% w/w.

In some embodiments, antibody to Telomerase RT is present in compositions of the present invention at concentrations of at least from about 0.000001% w/w to about 0.01% w/w; at least from about 0.000005% w/w to about 0.005% w/w; at least from about 0.00001% w/w to about 0.001% w/w; at least from about 0.00005% w/w to about 0.001% w/w, or at least from about 0.0001% w/w to about 0.001% w/w. In some embodiments, antibody to Telomerase RT is present in compositions of the present invention at concentrations of more than about 0.000001%; 0.000002%; 0.000003%; 0.000004%; 0.000005%; 0.000006%; 0.000007%; 0.000008%; 0.000009%; 0.00001%; 0.00002%; 0.00003%; 0.00004%; 0.00005%; 0.00006%; 0.00007%; 0.00008%; 0.00009%; 0.0001%; 0.0002%; 0.0003%; 0.0004%; 0.0005%; 0.0006%; 0.0007%; 0.0008%; 0.0009%; 0.001%; 0.002%; 0.003%; 0.004%; 0.005%; 0.006%; 0.007%; 0.008%; 0.009%, or 0.01% w/w. In some embodiments, antibody to Telomerase RT is present in compositions of the present invention at concentrations of less than about 0.01%; 0.009%; 0.008%; 0.007%; 0.006%; 0.005%; 0.004%; 0.003%; 0.002%; 0.001%; 0.0009%; 0.0008%; 0.0007%; 0.0006%; 0.0005%; 0.0004%; 0.0003%; 0.0002%; 0.0001%; 0.00009%; 0.00008%; 0.00007%; 0.00006%; 0.00005%; 0.00004%; 0.00003%; 0.00002%; 0.00001%; 0.000009%;

0.000008%; 0.000007%; 0.000006%; 0.000005%; 0.000004%; 0.000003%; 0.000002%; or 0.000001% w/w.

In some embodiments, EGF is present in compositions of the present invention at concentrations of at least from about 0.000001% w/w to about 0.001% w/w; at least from about 0.000001% w/w to about 0.0005% w/w; at least from about 0.000001% w/w to about 0.0001% w/w; or at least from about 0.000001% w/w to about 0.005% w/w. In some embodiments, EGF is present in compositions of the present invention at concentrations of at least about 0.000001%; 0.0000015%; 0.000002%; 0.0000025%; 0.000003%; 0.0000035%; 0.000004%; 0.0000045%; 0.000005%; 0.0000055%; 0.000006%; 0.0000065%; 0.000007%; 0.0000075%; 0.000008%; 0.0000085%; 0.000009%; 0.0000095%; 0.00001%; 0.000015%; 0.00002%; 0.000025%; 0.00003%; 0.000035%; 0.00004%; 0.000045%; 0.00005%; 0.000055%; 0.00006%; 0.000065%; 0.00007%; 0.000075%; 0.00008%; 0.000085%; 0.00009%; 0.000095%; 0.0001%; 0.00015%; 0.0002%; 0.00025%; 0.0003%; 0.00035%; 0.0004%; 0.00045%; 0.0005%; 0.00055% 0.0006%; 0.00065%; 0.0007%; 0.00075%; 0.0008%; 0.00085%; 0.0009%; 0.00095%; or 0.001% w/w. In some embodiments, EGF is present in compositions of the present invention at concentrations of less than about 0.001%; 0.00095%; 0.0009%; 0.00085%; 0.0008%; 0.00075%; 0.0007%; 0.00065%; 0.0006%; 0.00055%; 0.0005%; 0.00045%; 0.0004%; 0.00035%; 0.0003%; 0.00025%; 0.0002%; 0.00015%; 0.000095%; 0.00009%; 0.000085%; 0.00008%; 0.000075%; 0.00007%; 0.000065%; 0.00006%; 0.000055%; 0.00005%; 0.000045%; 0.00004%; 0.000035%; 0.00003%; 0.000025%; 0.00002%; 0.000015%; or 0.00001% w/w.

In some embodiments, VEGF is present in compositions of the present invention at concentrations of at least from about 0.000001% w/w to about 0.001% w/w; at least from about 0.000001% w/w to about 0.0005% w/w; at least from about 0.000001% w/w to about 0.0001% w/w; or at least from about 0.000001% w/w to about 0.005% w/w. In some embodiments, VEGF is present in compositions of the present invention at concentrations of at least about 0.000001%; 0.0000015%; 0.000002%; 0.0000025%; 0.000003%; 0.0000035%; 0.000004%; 0.0000045%; 0.000005%; 0.0000055%; 0.000006%; 0.0000065%; 0.000007%; 0.0000075%; 0.000008%; 0.0000085%; 0.000009%; 0.0000095%; 0.00001%; 0.000015%; 0.00002%; 0.000025%; 0.00003%; 0.000035%; 0.00004%; 0.000045%; 0.00005%; 0.000055%; 0.00006%; 0.000065%; 0.00007%; 0.000075%; 0.00008%; 0.000085%; 0.00009%; 0.000095%; 0.0001%; 0.00015%; 0.0002%; 0.00025%; 0.0003%; 0.00035%; 0.0004%; 0.00045%; 0.0005%; 0.00055% 0.0006%; 0.00065%; 0.0007%; 0.00075%; 0.0008%; 0.00085%; 0.0009%; 0.00095%; or 0.001% w/w. In some embodiments, VEGF is present in compositions of the present invention at concentrations of less than about 0.001%; 0.00095%; 0.0009%; 0.00085%; 0.0008%; 0.00075%; 0.0007%; 0.00065%; 0.0006%; 0.00055%; 0.0005%; 0.00045%; 0.0004%; 0.00035%; 0.0003%; 0.00025%; 0.0002%; 0.00015%; 0.000095%; 0.00009%; 0.000085%; 0.00008%; 0.000075%; 0.00007%; 0.000065%; 0.00006%; 0.000055%; 0.00005%; 0.000045%; 0.00004%; 0.000035%; 0.00003%; 0.000025%; 0.00002%; 0.000015%; 0.00001%; 0.000009%; 0.000008%; 0.000007%; 0.000006%; 0.000005%; 0.000004%; 0.000003%; 0.000002%; or 0.000001% w/w.

In some embodiments, a FGF is present in the compositions of the present invention at concentrations of at least from about 0.000001% w/w to about 0.01% w/w; at least from about 0.000001% w/w to about 0.001% w/w; or at least from about 0.000001% w/w to about 0.0001% w/w. In some embodiments, a FGF is present in the compositions of the present invention at concentrations of at least about 0.000001%; 0.0000015%; 0.000002%; 0.0000025%; 0.000003%; 0.0000035%; 0.000004%; 0.0000045%; 0.000005%; 0.0000055%; 0.000006%; 0.0000065%; 0.000007%; 0.0000075%; 0.000008%; 0.0000085%; 0.000009%; 0.0000095%; 0.00001%; 0.000015%; 0.00002%; 0.000025%; 0.00003%; 0.000035%; 0.00004%; 0.000045%; 0.00005%; 0.000055%; 0.00006%; 0.000065%; 0.00007%; 0.000075%; 0.00008%; 0.000085%; 0.00009%; 0.000095%; 0.0001%; 0.00015%; 0.0002%; 0.00025%; 0.0003%; 0.00035%; 0.0004%; 0.00045%; 0.0005%; 0.00055% 0.0006%; 0.00065%; 0.0007%; 0.00075%; 0.0008%; 0.00085%; 0.0009%; 0.00095%; or 0.001% w/w. In some embodiments, a FGF is present in the compositions at concentrations less than about 0.01%; 0.009%; 0.008%; 0.007%; 0.006%; 0.005%; 0.004%; 0.003%; 0.002%; 0.001%; 0.00095%; 0.0009%; 0.00085%; 0.0008%; 0.00075%; 0.0007%; 0.00065%; 0.0006%; 0.00055%; 0.0005%; 0.00045%; 0.0004%; 0.00035%; 0.0003%; 0.00025%; 0.0002%; 0.00015%; 0.000095%; 0.00009%; 0.000085%; 0.00008%; 0.000075%; 0.00007%; 0.000065%; 0.00006%; 0.000055%; 0.00005%; 0.000045%; 0.00004%; 0.000035%; 0.00003%; 0.000025%; 0.00002%; 0.000015%; 0.00001%; 0.000009%; 0.000008%; 0.000007%; 0.000006%; 0.000005%; 0.000004%; 0.000003%; 0.000002%; or 0.000001% w/w. In some embodiments, more than one FGF is present in the compositions of the present invention, each independently at concentrations of at least from about 0.000001% w/w to about 0.01% w/w; at least from about 0.000001% w/w to about 0.001% w/w; or at least from about 0.000001% w/w to about 0.0001% w/w. More than one FGF may be present in the compositions of the present invention, each independently at concentrations of at least about 0.000001%; 0.0000015%; 0.000002%; 0.0000025%; 0.000003%; 0.0000035%; 0.000004%; 0.0000045%; 0.000005%; 0.0000055%; 0.000006%; 0.0000065%; 0.000007%; 0.0000075%; 0.000008%; 0.0000085%; 0.000009%; 0.0000095%; 0.00001%; 0.000015%; 0.00002%; 0.000025%; 0.00003%; 0.000035%; 0.00004%; 0.000045%; 0.00005%; 0.000055%; 0.00006%; 0.000065%; 0.00007%; 0.000075%; 0.00008%; 0.000085%; 0.00009%; 0.000095%; 0.0001%; 0.00015%; 0.0002%; 0.00025%; 0.0003%; 0.00035%; 0.0004%; 0.00045%; 0.0005%; 0.00055% 0.0006%; 0.00065%; 0.0007%; 0.00075%; 0.0008%; 0.00085%; 0.0009%; 0.00095%; or 0.001% w/w. In some embodiments, more than one FGF is present in the compositions, each independently at concentrations less than about 0.01%; 0.009%; 0.008%; 0.007%; 0.006%; 0.005%; 0.004%; 0.003%; 0.002%; 0.001%; 0.00095%; 0.0009%; 0.00085%; 0.0008%; 0.00075%; 0.0007%; 0.00065%; 0.0006%; 0.00055%; 0.0005%; 0.00045%; 0.0004%; 0.00035%; 0.0003%; 0.00025%; 0.0002%; 0.00015%; 0.000095%; 0.00009%; 0.000085%; 0.00008%; 0.000075%; 0.00007%; 0.000065%; 0.00006%; 0.000055%; 0.00005%; 0.000045%; 0.00004%; 0.000035%; 0.00003%; 0.000025%; 0.00002%; 0.000015%; 0.00001%; 0.000009%; 0.000008%; 0.000007%; 0.000006%; 0.000005%; 0.000004%; 0.000003%; 0.000002%; or 0.000001% w/w.

In some embodiments, KGF-1 is present in the compositions of the present invention at concentrations of at least from about 0.000001% w/w to about 0.01% w/w; at least from about 0.000001% w/w to about 0.001% w/w; or at least from about 0.000001% w/w to about 0.0001% w/w. In some embodiments, KGF-1 is present in the compositions of the present invention at concentrations of at least about 0.000001%; 0.0000015%; 0.000002%; 0.0000025%; 0.000003%; 0.0000035%; 0.000004%; 0.0000045%; 0.000005%; 0.0000055%; 0.000006%; 0.0000065%; 0.000007%; 0.0000075%; 0.000008%; 0.0000085%; 0.000009%; 0.0000095%; 0.00001%; 0.000015%; 0.00002%; 0.000025%; 0.00003%; 0.000035%; 0.00004%; 0.000045%; 0.00005%; 0.000055%; 0.00006%; 0.000065%; 0.00007%; 0.000075%; 0.00008%; 0.000085%; 0.00009%; 0.000095%; 0.0001%; 0.00015%; 0.0002%; 0.00025%; 0.0003%; 0.00035%; 0.0004%; 0.00045%; 0.0005%; 0.00055% 0.0006%; 0.00065%; 0.0007%; 0.00075%; 0.0008%; 0.00085%; 0.0009%; 0.00095%; or 0.001% w/w. In other embodiments, KGF-1 is present in the compositions at concentrations less than about 0.01%; 0.009%; 0.008%; 0.007%; 0.006%; 0.005%; 0.004%; 0.003%; 0.002%; 0.001%; 0.00095%; 0.0009%; 0.00085%; 0.0008%; 0.00075%; 0.0007%; 0.00065%; 0.0006%; 0.00055%; 0.0005%; 0.00045%; 0.0004%; 0.00035%; 0.0003%; 0.00025%; 0.0002%; 0.00015%; 0.000095%; 0.00009%; 0.000085%; 0.00008%; 0.000075%; 0.00007%; 0.000065%; 0.00006%; 0.000055%; 0.00005%; 0.000045%; 0.00004%; 0.000035%; 0.00003%; 0.000025%; 0.00002%; 0.000015%; 0.00001%; 0.000009%; 0.000008%; 0.000007%; 0.000006%; 0.000005%; 0.000004%; 0.000003%; 0.000002%; or 0.000001% w/w.

In some embodiments, KGF-2 is present in the compositions of the present invention at concentrations of at least from about 0.000001% w/w to about 0.01% w/w; at least from about 0.000001% w/w to about 0.001% w/w; or at least from about 0.000001% w/w to about 0.0001% w/w. In other embodiments, KGF-2 is present in the compositions of the present invention at concentrations of at least about 0.000001%; 0.0000015%; 0.000002%; 0.0000025%; 0.000003%; 0.0000035%; 0.000004%; 0.0000045%; 0.000005%; 0.0000055%; 0.000006%; 0.0000065%; 0.000007%; 0.0000075%; 0.000008%; 0.0000085%; 0.000009%; 0.0000095%; 0.00001%; 0.000015%; 0.00002%; 0.000025%; 0.00003%; 0.000035%; 0.00004%; 0.000045%; 0.00005%; 0.000055%; 0.00006%; 0.000065%; 0.00007%; 0.000075%; 0.00008%; 0.000085%; 0.00009%; 0.000095%; 0.0001%; 0.00015%; 0.0002%; 0.00025%; 0.0003%; 0.00035%; 0.0004%; 0.00045%; 0.0005%; 0.00055% 0.0006%; 0.00065%; 0.0007%; 0.00075%; 0.0008%; 0.00085%; 0.0009%; 0.00095%; or 0.001% w/w. In yet other embodiments, KGF-2 is present in the compositions at concentrations less than about 0.01%; 0.009%; 0.008%; 0.007%; 0.006%; 0.005%; 0.004%; 0.003%; 0.002%; 0.001%; 0.00095%; 0.0009%; 0.00085%; 0.0008%; 0.00075%; 0.0007%; 0.00065%; 0.0006%; 0.00055%; 0.0005%; 0.00045%; 0.0004%; 0.00035%; 0.0003%; 0.00025%; 0.0002%; 0.00015%; 0.000095%; 0.00009%; 0.000085%; 0.00008%; 0.000075%; 0.00007%; 0.000065%; 0.00006%; 0.000055%; 0.00005%; 0.000045%; 0.00004%; 0.000035%; 0.00003%; 0.000025%; 0.00002%; 0.000015%; 0.00001%; 0.000009%; 0.000008%; 0.000007%; 0.000006%; 0.000005%; 0.000004%; 0.000003%; 0.000002%; or 0.000001% w/w.

In some embodiments, Transforming Growth Factor-β1 is present in compositions of the present invention at concentrations of at least from about 0.000001% w/w to about 0.001% w/w; at least from about 0.000001% w/w to about 0.0005% w/w; at least from about 0.000001% w/w to about 0.0001% w/w; or at least from about 0.000001% w/w to about 0.0001% w/w. In some embodiments, Transforming Growth Factor-β1 is present in compositions of the present invention at concentrations of at least about 0.000001%; 0.0000015%; 0.000002%; 0.0000025%; 0.000003%; 0.0000035%; 0.000004%; 0.0000045%; 0.000005%; 0.0000055%; 0.000006%; 0.0000065%; 0.000007%; 0.0000075%; 0.000008%; 0.0000085%; 0.000009%; 0.0000095%; 0.00001%; 0.000015%; 0.00002%; 0.000025%; 0.00003%; 0.000035%; 0.00004%; 0.000045%; 0.00005%; 0.000055%; 0.00006%; 0.000065%; 0.00007%; 0.000075%; 0.00008%; 0.000085%; 0.00009%; 0.000095%; 0.0001%; 0.00015%; 0.0002%; 0.00025%; 0.0003%; 0.00035%; 0.0004%; 0.00045%; 0.0005%; 0.00055% 0.0006%; 0.00065%; 0.0007%; 0.00075%; 0.0008%; 0.00085%; 0.0009%; 0.00095%; or 0.001% w/w. In some embodiments, Transforming Growth Factor-β1 is present in compositions of the present invention at concentrations of less than about 0.001%; 0.00095%; 0.0009%; 0.00085%; 0.0008%; 0.00075%; 0.0007%; 0.00065%; 0.0006%; 0.00055%; 0.0005%; 0.00045%; 0.0004%; 0.00035%; 0.0003%; 0.00025%; 0.0002%; 0.00015%; 0.000095%; 0.00009%; 0.000085%; 0.00008%; 0.000075%; 0.00007%; 0.000065%; 0.00006%; 0.000055%; 0.00005%; 0.000045%; 0.00004%; 0.000035%; 0.00003%; 0.000025%; 0.00002%; 0.000015%; or 0.00001% w/w.

In some embodiments, a myristoylated peptide is present in the compositions of the invention at concentrations of at least from about 0.001% w/w to about 2.0% w/w; at least from about 0.01% w/w to about 2.0% w/w; at least from about 0.05% w/w to about 2.0% w/w or at least from about 0.01% w/w to about 2.0% w/w. In some embodiments, a myristoylated peptide is present in the compositions of the invention at concentrations of at least about 0.001%; 0.002%; 0.003%; 0.004%; 0.005%; 0.006%; 0.007%; 0.008%; 0.009%; 0.01%; 0.02%; 0.03%; 0.04%; 0.05%; 0.06%; 0.07%; 0.08%; 0.09%; 0.10%; 0.15%; 0.20%; 0.25%; 0.30%; 0.35%; 0.40%; 0.45%; 0.50%; 0.55%; 0.60%; 0.65%; 0.70%; 0.75%; 0.80%; 0.85%; 0.90%; 0.95%; 1.00%; 1.10%; 1.20%; 1.30%; 1.40%; 1.45%; 1.50%; 1.60%; 1.70%; 1.80%; 1.90% or 2.00% w/w. In some embodiments, a myristoylated peptide is present in the compositions of the invention at concentrations less than about 2.00%; 1.90%; 1.80%; 1.70%; 1.60%; 1.50%; 1.40%; 1.370%; 1.20%; 1.10%; 1.00%; 0.90%; 0.85%; 0.80%; 0.75%; 0.70%; 0.65%; 0.60%; 0.55%; 0.50%; 0.45%; 0.40%; 0.35%; 0.30%; 0.25%; 0.20%; 0.15%; 0.10%; 0.05%; 0.001%, 0.009%; 0.008%; 0.007%; 0.006%; 0.005%; 0.004%; 0.003%; 0.002%; or 0.0001% w/w. In some embodiments, more than one myristoylated peptide is present in the compositions of the inventions, each independently at concentrations of at least from about 0.001% w/w to about 2.0% w/w; at least from about 0.01% w/w to about 2.0% w/w; at least from about 0.05% w/w to about 2.0% w/w or at least from about 0.01% w/w to about 2.0% w/w. In some embodiments, more than one myristoylated peptide is present in the compositions of the invention, each independently at concentrations of at least about 0.001%; 0.002%; 0.003%; 0.004%; 0.005%; 0.006%; 0.007%; 0.008%; 0.009%; 0.01%; 0.02%; 0.03%; 0.04%; 0.05%; 0.06%; 0.07%; 0.08%; 0.09%; 0.10%; 0.15%; 0.20%; 0.25%; 0.30%; 0.35%; 0.40%; 0.45%; 0.50%; 0.55%; 0.60%; 0.65%; 0.70%; 0.75%; 0.80%; 0.85%; 0.90%; 0.95%; 1.00%; 1.10%; 1.20%; 1.30%; 1.40%; 1.45%; 1.50%; 1.60%; 1.70%; 1.80%; 1.90% or 2.00% w/w. In some embodiments, more than one myristoylated peptide is present in the compositions of the invention, each independently at concentrations less than about 2.00%; 1.90%; 1.80%; 1.70%; 1.60%; 1.50%; 1.40%; 1.370%; 1.20%; 1.10%; 1.00%; 0.90%; 0.85%; 0.80%; 0.75%; 0.70%; 0.65%; 0.60%; 0.55%; 0.50%; 0.45%; 0.40%; 0.35%; 0.30%; 0.25%; 0.20%; 0.15%; 0.10%; 0.05%; 0.001%; 0.009%; 0.008%; 0.007%; 0.006%; 0.005%; 0.004%; 0.003%; 0.002%; or 0.0001% w/w.

A palmitoylated peptide may be present in the compositions of the present invention at concentrations of at least from about 0.50% w/w to about 6.00% w/w. In some embodiments, a palmitoylated peptide is present in the compositions of the invention at concentrations of at least about 0.50%; 0.60%; 0.70%; 0.80%; 0.90%; 1.10%; 1.20%; 1.30%; 1.40%; 1.50%; 1.60%; 1.70%; 1.80%; 1.90%; 2.00%; 2.10%; 2.20%; 2.30%; 2.40%; 2.50%; 2.60%; 2.70%; 2.80%; 2.90%; 3.00%; 3.10%; 3.20%; 3.30%; 3.40%; 3.50%; 3.60%; 3.70%; 3.80%; 3.90%; 4.00%; 4.10%; 4.20%; 4.30%; 4.40%; 4.50%; 4.60%; 4.70%; 4.80%; 4.90%; 5.00%; 5.10%; 5.20%; 5.30%; 5.40%; 5.50%; 5.60%; 5.70%; 5.80%; 5.90% or 6.00% w/w. In some embodiments, a palmitoylated peptide is present in the compositions of the invention at concentrations of less than about 6.00%; 5.90%; 5.80%; 5.70%; 5.60%; 5.50%; 5.40%; 5.30%; 5.20%; 5.10%; 5.00%; 4.90%; 4.80%; 4.70%; 4.60%; 4.50%; 4.40%; 4.30%; 4.20%; 4.10%; 4.00%; 3.90%; 3.80%; 3.70%; 3.60%; 3.50%; 3.40%; 3.30%; 3.20%; 3.10%; 3.00%; 2.90%; 2.90%; 2.80%; 2.70%; 2.60%; 2.50%; 240%; 2.30%; 2.20%; 2.10%; 2.00%; 1.90%; 1.80%; 1.70%; 1.60%; 1.50%; 1.40%; 1.30%; 1.20%; 1.10%; 1.00%; 0.90%; 0.80%; 0.70%; 0.60%; or 0.50% w/w. In some embodiments, more than one palmitoylated peptide is present in the compositions of the invention each independently at concentrations of at least about 0.50%; 0.60%; 0.70%; 0.80%; 0.90%; 1.10%; 1.20%; 1.30%; 1.40%; 1.50%; 1.60%; 1.70%; 1.80%; 1.90%; 2.00%; 2.10%; 2.20%; 2.30%; 2.40%; 2.50%; 2.60%; 2.70%; 2.80%; 2.90%; 3.00%; 3.10%; 3.20%; 3.30%; 3.40%; 3.50%; 3.60%; 3.70%; 3.80%; 3.90%; 4.00%; 4.10%; 4.20%; 4.30%; 4.40%; 4.50%; 4.60%; 4.70%; 4.80%; 4.90%; 5.00%; 5.10%; 5.20%; 5.30%; 5.40%; 5.50%; 5.60%; 5.70%; 5.80%; 5.90% or 6.00% w/w. In some embodiments, more than one palmitoylated peptide is present in the compositions of the invention, each independently at concentrations of less than about 6.00%; 5.90%; 5.80%; 5.70%; 5.60%; 5.50%; 5.40%; 5.30%; 5.20%; 5.10%; 5.00%; 4.90%; 4.80%; 4.70%; 4.60%; 4.50%; 4.40%; 4.30%; 4.20%; 4.10%; 4.00%; 3.90%; 3.80%; 3.70%; 3.60%; 3.50%; 3.40%; 3.30%; 3.20%; 3.10%; 3.00%; 2.90%; 2.90%; 2.80%; 2.70%; 2.60%; 2.50%; 240%; 2.30%; 2.20%; 2.10%; 2.00%; 1.90%; 1.80%; 1.70%; 1.60%; 1.50%; 1.40%; 1.30%; 1.20%; 1.10%; 1.00%; 0.90%; 0.80%; 0.70%; 0.60%; or 0.50% w/w.

In some embodiments, one or more antioxidants are present in the compositions of the invention, each independently at concentrations present in the compositions of the invention at concentrations of at least from about 0.001% w/w to about 2.0% w/w; at least from about 0.01% w/w to about 2.0% w/w; at least from about 0.05% w/w to about 2.0% w/w or at least from about 0.01% w/w to about 2.0% w/w. In some embodiments, one or more antioxidants are present in the compositions of the invention, each independently at concentrations of at least about 0.001%; 0.002%; 0.003%; 0.004%; 0.005%; 0.006%; 0.007%; 0.008%; 0.009%; 0.01%; 0.02%; 0.03%; 0.04%; 0.05%; 0.06%; 0.07%; 0.08%; 0.09%; 0.10%; 0.15%; 0.20%; 0.25%; 0.30%; 0.35%; 0.40%; 0.45%; 0.50%; 0.55%; 0.60%; 0.65%; 0.70%; 0.75%; 0.80%; 0.85%; 0.90%; 0.95%; 1.00%; 1.10%; 1.20%; 1.30%; 1.40%; 1.45%; 1.50%; 1.60%; 1.70%; 1.80%; 1.90%; or 2.00% w/w. In some embodiments, one or more antioxidants are present in the compositions of the invention, each independently at concentrations less than about 2.00%; 1.90%; 1.80%; 1.70%; 1.60%; 1.50%; 1.40%; 1.370%; 1.20%; 1.10%; 1.00%; 0.90%; 0.85%; 0.80%; 0.75%; 0.70%; 0.65%; 0.60%; 0.55%; 0.50%; 0.45%; 0.40%; 0.35%; 0.30%; 0.25%; 0.20%; 0.15%; 0.10%; 0.05%; 0.001%; 0.009%; 0.008%; 0.007%; 0.006%; 0.005%; 0.004%; 0.003%; 0.002%; or 0.0001% w/w.

In some embodiments, ubiquinone is present in the compositions of the invention at concentrations present in the compositions of the invention at concentrations of at least from about 0.001% w/w to about 2.0% w/w; at least from about 0.01% w/w to about 2.0% w/w; at least from about 0.05% w/w to about 2.0% w/w or at least from about 0.01% w/w to about 2.0% w/w. In some embodiments, ubiquinone is present in the compositions of the invention, at concentrations of at least about 0.001%; 0.002%; 0.003%; 0.004%; 0.005%; 0.006%; 0.007%; 0.008%; 0.009%; 0.01%; 0.02%; 0.03%; 0.04%; 0.05%; 0.06%; 0.07%; 0.08%; 0.09%; 0.10%; 0.15%; 0.20%; 0.25%; 0.30%; 0.35%; 0.40%; 0.45%; 0.50%; 0.55%; 0.60%; 0.65%; 0.70%; 0.75%; 0.80%; 0.85%; 0.90%; 0.95%; 1.00%; 1.10%; 1.20%; 1.30%; 1.40%; 1.45%; 1.50%; 1.60%; 1.70%; 1.80%; 1.90%; or 2.00% w/w. In some embodiments, ubiquinone is present in the compositions of the invention at concentrations less than about 2.00%; 1.90%; 1.80%; 1.70%; 1.60%; 1.50%; 1.40%; 1.370%; 1.20%; 1.10%; 1.00%; 0.90%; 0.85%; 0.80%; 0.75%; 0.70%; 0.65%; 0.60%; 0.55%; 0.50%; 0.45%; 0.40%; 0.35%; 0.30%; 0.25%; 0.20%; 0.15%; 0.10%; 0.05%; 0.001%; 0.009%; 0.008%; 0.007%; 0.006%; 0.005%; 0.004%; 0.003%; 0.002%; or 0.0001% w/w.

In some embodiments, green tea extract is present in the compositions of the invention at concentrations present in the compositions of the invention at concentrations of at least from about 0.001% w/w to about 2.0% w/w; at least from about 0.01% w/w to about 2.0% w/w; at least from about 0.05% w/w to about 2.0% w/w or at least from about 0.01% w/w to about 2.0% w/w. In some embodiments, green tea extract is present in the compositions of the invention, at concentrations of at least about 0.001%; 0.002%; 0.003%; 0.004%; 0.005%; 0.006%; 0.007%; 0.008%; 0.009%; 0.01%; 0.02%; 0.03%; 0.04%; 0.05%; 0.06%; 0.07%; 0.08%; 0.09%; 0.10%; 0.15%; 0.20%; 0.25%; 0.30%; 0.35%; 0.40%; 0.45%; 0.50%; 0.55%; 0.60%; 0.65%; 0.70%; 0.75%; 0.80%; 0.85%; 0.90%; 0.95%; 1.00%; 1.10%; 1.20%; 1.30%; 1.40%; 1.45%; 1.50%; 1.60%; 1.70%; 1.80%; 1.90%; or 2.00% w/w. In some embodiments, green tea extract is present in the compositions of the invention at concentrations less than about 2.00%; 1.90%; 1.80%; 1.70%; 1.60%; 1.50%; 1.40%; 1.370%; 1.20%; 1.10%; 1.00%; 0.90%; 0.85%; 0.80%; 0.75%; 0.70%; 0.65%; 0.60%; 0.55%; 0.50%; 0.45%; 0.40%; 0.35%; 0.30%; 0.25%; 0.20%; 0.15%; 0.10%; 0.05%; 0.001%; 0.009%; 0.008%; 0.007%; 0.006%; 0.005%; 0.004%; 0.003%; 0.002%; or 0.0001% w/w.

The compositions of the present invention may contain a wide range of additional components. These include emollients, film forming agents, emulsifiers, thickening agents and other rheological modifiers. Fragrance and coloring agents may also be included. The CTFA Cosmetic Ingredient Handbook, Seventh Edition, 1997 and the Eighth Edition, 2000, which are incorporated by reference herein in their entirety, describes a wide variety of ingredients commonly used in skin care compositions, which are suitable for use in the compositions of the present invention. Other topically-applied compounds are listed in Remington's Pharmaceutical Sciences, 20th Ed., Lippincott Williams & Witkins, Baltimore, Md. (2000) (hereinafter Remington's), U.S. Pharmacopeia and National Formulary, The United States Pharmacopeial Convention, Inc., Rockville, Md. and Physician's Desk Reference, Medical Economics Co., Inc., Oradell, N.J. incorporated herein by reference. The concentration of the other active ingredient in formulations provided by the invention is that which provides an effective amount of the other active ingredient; these concentrations are well-known in the art. See, e.g., the above references, as well as Textbook of Dermatology, Champion, Burton, Burns, and Bretnach, eds., Blackwell Publishing, 1998. Further examples of cosmetic and/or pharmaceutical ingredients which are suitable for use in compositions of the present invention are disclosed in U.S. Patent Publication Nos. 2004/0180020, 2005/0142095 and U.S. Pat. No. 6,277,892.

III. Methods of Administration

Compositions according to the present invention may be applied to the skin in any number of forms or vehicles known to those of skill in the art including: (i) aqueous, aqueous-alcoholic or oily solutions, optionally gelled; (ii) emulsions obtained by dispersing an aqueous phase in an oil or silicone phase, or vice versa (i.e., water-in-oil, oil-in-water, water-in-silicone, silicone-in-water); (iii) triple emulsions (i.e., water-in-oil-in-water or oil-in-water-in-oil); or (iv) vesicular dispersions. The viscosity of the final formulation may be modulated by methods known in the art to form a cream, lotion, gel, serum or spray. Any form of applicator known in the art is also included in the methods of administering the compositions of the invention.

IV. Methods of Use

One aspect of the present invention is directed to a method for reducing the appearance of biological and/or environmentally-caused aging by topically-applying to the skin of a human, a dermatological or cosmetic composition comprising: (a) telomerase; (a) a telomerase; (b) one or more growth factors; (c) at least two acylated peptides; and (d) optionally, at least one skin benefit agent selected from the group consisting of antioxidants, humectants and moisturizing agents. In other embodiments of the methods of use, the composition contains an Epidermal Growth Factor, at least one Keratinocyte Growth Factor, Transforming Growth Factor-$\beta$1, and a telomerase, which provides surprisingly efficacious use in topical treatment of skin. In yet other embodiments the methods of use, the composition contains an Epidermal Growth Factor, at least one Keratinocyte Growth Factor, Transforming Growth Factor-$\beta$1, and an antibody to telomerase, which provides surprisingly efficacious use in topical treatment of skin.

In some embodiments of the invention, the compositions described herein are applied topically to the skin of a human to reduce inflammation from either intrinsic or extrinsic sources. In other embodiments of the invention, the compositions described herein are applied topically to the skin of a human to reduce oxidative stress from either extrinsic or intrinsic sources. In other embodiments of the invention, the compositions described herein are applied topically to the skin of a human to produce a skin brightening effect. In other embodiments of the invention, the compositions described herein are applied topically to the skin of a human to reduce fine lines and wrinkles in skin. In some other embodiments of the invention, the compositions described herein are applied topically to the skin of a human to enhance elasticity of skin. In other embodiments of the invention, the compositions described herein are applied topically to the skin of a human to reduce the appearance of scarring and lesions of the skin due to extrinsic and intrinsic factors As used in the present invention, by the phrase "signs of biological or environmentally-caused aging biological or environmentally-caused aging" is meant fine lines, wrinkles, furrows, age spots and/or reduced skin elasticity. Reduction in the appearance of fine lines and wrinkles can be measured by a number of techniques known to those of skill in the art and including clinical assessment by a trained observer (e.g., doctor, nurse, technician) or instrumentally (e.g., by use of Silflo replica masks or an imaging system such as VISTA from Canfield Scientific.)

Topical application may be more than about once, twice, three times, four times, five times, or six times per week, or more than once, twice, three times, four times, five times, or six times per day. Frequency of application may be less than about twice, three times, four times, five times, or six times per week, or less than about once, twice, three times, four times, five times, or six times per day. Some embodiments of the invention provide a method for cosmetic treatment of the skin of an individual by topical administration of an effective amount of the composition of the invention. In some embodiments, the composition is administered an average of about once per day; in some embodiments, the composition is administered an average of about once or twice per day; in some embodiments, the composition is administered an average of about once to three times per day; in some embodiments, the composition is administered an average of more than about three times per day. In one embodiment, the composition is administered an average of about twice per day, typically in the morning upon rising and in the evening before retiring.

V. Kits

In still another aspect, the present invention provides kits for the cosmetic treatment of skin or to produce a desired cosmetic result. These kits comprise the compositions described herein, in a container or containers which are held in suitable packaging. In some embodiments the kits further contain instructions teaching the use of the kit according to the various methods and approaches described herein. Such kits may also include information, such as scientific literature references, package insert materials, cosmetic trial results, and/or summaries of these and the like, which indicate or establish the activities and/or advantages of the composition. Such information may be based on the results of various studies, for example, studies using experimental animals involving in vivo models and studies based on human cosmetic or clinical trials. Kits described herein can be provided, marketed and/or promoted to health care providers (e.g., dermatologists and other physicians), skin care appearance care providers, including cosmetologists, hair stylists, and the like. Kits for cosmetic use may also be provided, marketed and/or promoted directly to consumers. Kits may be marketed in spas and retail outlets.

VI. Examples

The components and specific ingredients are exemplary only, and do not limit the modifications which can be made within the scope of the invention.

Example 1

Skin Care Composition I

TABLE I

| INGREDIENT | w/w % |
| --- | --- |
| D.I. WATER | Q.S. to 100% |
| ALLANTOIN | 0.10 |
| PANTHENOL | 1.00 |
| BUTYLENE GLYCOL | 2.00 |

TABLE I-continued

| INGREDIENT | w/w % |
|---|---|
| MAGNESIUM ALUMINUM SILICATE | 0.30 |
| XANTHAN GUM | 0.30 |
| GLYCERIN | 3.00 |
| CETEARYL ALCOHOL | 2.50 |
| CETEARETH 20 | |
| GLYCERYL STEARATE | 1.00 |
| SUNFLOWER OIL | 3.50 + 0.50 |
| MEADOWFOAM SEED OIL | 1.00 |
| SHEA BUTTER | 1.00 |
| MANGO BUTTER | 0.50 |
| AVOCADO BUTTER | 0.50 |
| DIMETHICONE | 2.00 |
| LINOLEIC ACID, | 0.25 |
| LINOLENIC ACID, | |
| TOCOPHEROL | |
| DL-ALPHA TOCOPHERYL ACETATE | 0.001 |
| PHENOXYETHANOL | 1.00 |
| METHYLPARABEN | |
| BUTYLPARABEN | |
| PROPYLPARABEN | |
| ETHYLPARABEN | |
| SODIUM HYALURONATE | 1.00 |
| JAPANESE GREEN TEA EXTRACT | 0.50 |
| METHYLSILANOL MANNURONATE | 1.00 |
| CYCLOPENTASILOXANE | 0.50 |
| DIMETHICONE/VINYL DIMETHICONE | |
| CROSSPOLYMER | |
| UBIQUINONE | 0.30 |
| CERAMIDES | 3.00 |
| PEG-40 HYDROGENATED CASTOR OIL | |
| PALMITOYL PENTAPEPTIDE-4 | 3.00 |
| MYRISTOYL PENTAPEPTIDE -8 | 0.50 |
| MYRISTOYL PENTAPEPTIDE -11 | 0.50 |
| HUMAN TELOMERASE REVERSE TRANSCRIPTASE | 0.0006 |
| KGF-1 | 0.00006 |
| EGF | 0.00015 |
| TGF-β1 | 0.00002 |

Example 2

Skin Care Composition II

TABLE II

| INGREDIENT | w/w % |
|---|---|
| D.I. WATER | Q.S. to 100% |
| ALLANTOIN | 0.10 |
| PANTHENOL | 1.00 |
| BUTYLENE GLYCOL | 2.00 |
| MAGNESIUM ALUMINUM SILICATE | 0.30 |
| XANTHAN GUM | 0.30 |
| GLYCERIN | 3.00 |
| CETEARYL ALCOHOL | 2.50 |
| CETEARETH 20 | |
| GLYCERYL STEARATE | 1.00 |
| SUNFLOWER OIL | 3.50 + 0.50 |
| MEADOWFOAM SEED OIL | 1.00 |
| SHEA BUTTER | 1.00 |
| MANGO BUTTER | 0.50 |
| AVOCADO BUTTER | 0.50 |
| DIMETHICONE | 2.00 |
| LINOLEIC ACID, | 0.25 |
| LINOLENIC ACID, | |
| TOCOPHEROL | |
| DL-ALPHA TOCOPHERYL ACETATE | 0.001 |
| PHENOXYETHANOL | 1.00 |
| METHYLPARABEN | |
| BUTYLPARABEN | |
| PROPYLPARABEN | |
| ETHYLPARABEN | |
| SODIUM HYALURONATE | 1.00 |

TABLE II-continued

| INGREDIENT | w/w % |
|---|---|
| JAPANESE GREEN TEA EXTRACT | 0.50 |
| METHYLSILANOL MANNURONATE | 1.00 |
| CYCLOPENTASILOXANE | 0.50 |
| DIMETHICONE/VINYL DIMETHICONE | |
| CROSSPOLYMER | |
| UBIQUINONE | 0.30 |
| CERAMIDES | 3.00 |
| PEG-40 HYDROGENATED CASTOR OIL | |
| PALMITOYL PENTAPEPTIDE-4 | 3.00 |
| MYRISTOYL PENTAPEPTIDE -8 | 0.50 |
| MYRISTOYL PENTAPEPTIDE -11 | 0.50 |
| ANTIBODY TO HUMAN TELOMERASE REVERSE TRANSCRIPTASE | 0.0006 |
| KGF-1 | 0.00006 |
| EGF | 0.00015 |
| TGF-β1 | 0.00002 |

Example 3

Skin Care Composition III

TABLE III

| INGREDIENT | w/w % |
|---|---|
| D.I. WATER | Q.S. to 100% |
| ALLANTOIN | 0.10 |
| PANTHENOL | 1.00 |
| BUTYLENE GLYCOL | 2.00 |
| MAGNESIUM ALUMINUM SILICATE | 0.30 |
| XANTHAN GUM | 0.30 |
| GLYCERIN | 3.00 |
| CETEARYL ALCOHOL | 2.50 |
| CETEARETH 20 | |
| GLYCERYL STEARATE | 1.00 |
| SUNFLOWER OIL | 3.50 + 0.50 |
| MEADOWFOAM SEED OIL | 1.00 |
| SHEA BUTTER | 1.00 |
| MANGO BUTTER | 0.50 |
| AVOCADO BUTTER | 0.50 |
| DIMETHICONE | 2.00 |
| LINOLEIC ACID, | 0.25 |
| LINOLENIC ACID, | |
| TOCOPHEROL | |
| DL-ALPHA TOCOPHERYL ACETATE | 0.001 |
| PHENOXYETHANOL | 1.00 |
| METHYLPARABEN | |
| BUTYLPARABEN | |
| PROPYLPARABEN | |
| ETHYLPARABEN | |
| SODIUM HYALURONATE | 1.00 |
| JAPANESE GREEN TEA EXTRACT | 0.50 |
| METHYLSILANOL MANNURONATE | 1.00 |
| CYCLOPENTASILOXANE | 0.50 |
| DIMETHICONE/VINYL DIMETHICONE | |
| CROSSPOLYMER | |
| UBIQUINONE | 0.30 |
| CERAMIDES | 3.00 |
| PEG-40 HYDROGENATED CASTOR OIL | |
| PALMITOYL PENTAPEPTIDE-4 | 3.00 |
| MYRISTOYL PENTAPEPTIDE -8 | 0.50 |
| MYRISTOYL PENTAPEPTIDE -11 | 0.50 |
| HUMAN TELOMERASE REVERSE TRANSCRIPTASE and HUMAN TELOMERASE RNA | 0.0006 |
| KGF-1 | 0.00006 |
| EGF | 0.00015 |
| TGF-β1 | 0.00002 |

Example 4

Skin Care Composition IV

TABLE IV

| INGREDIENT | w/w % |
| --- | --- |
| D.I. WATER | Q.S. to 100% |
| ALLANTOIN | 0.10 |
| PANTHENOL | 1.00 |
| BUTYLENE GLYCOL | 2.00 |
| MAGNESIUM ALUMINUM SILICATE | 0.30 |
| XANTHAN GUM | 0.30 |
| GLYCERIN | 3.00 |
| CETEARYL ALCOHOL | 2.50 |
| CETEARETH 20 | |
| GLYCERYL STEARATE | 1.00 |
| SUNFLOWER OIL | 3.50 + 0.50 |
| MEADOWFOAM SEED OIL | 1.00 |
| SHEA BUTTER | 1.00 |
| MANGO BUTTER | 0.50 |
| AVOCADO BUTTER | 0.50 |
| DIMETHICONE | 2.00 |
| LINOLEIC ACID, LINOLENIC ACID, TOCOPHEROL | 0.25 |
| DL-ALPHA TOCOPHERYL ACETATE | 0.001 |
| PHENOXYETHANOL | 1.00 |
| METHYLPARABEN | |
| BUTYLPARABEN | |
| PROPYLPARABEN | |
| ETHYLPARABEN | |
| SODIUM HYALURONATE | 1.00 |
| JAPANESE GREEN TEA EXTRACT | 0.50 |
| METHYLSILANOL MANNURONATE | 1.00 |
| CYCLOPENTASILOXANE | 0.50 |
| DIMETHICONE/VINYL DIMETHICONE CROSSPOLYMER | |
| UBIQUINONE | 0.30 |
| CERAMIDES | 3.00 |
| PEG-40 HYDROGENATED CASTOR OIL | |
| PALMITOYL PENTAPEPTIDE-4 | 3.00 |
| MYRISTOYL PENTAPEPTIDE -8 | 0.50 |
| MYRISTOYL PENTAPEPTIDE -11 | 0.50 |
| HUMAN TELOMERASE REVERSE TRANSCRIPTASE and HUMAN TELOMERASE RNA | 0.0006 |
| KGF-1 | 0.00006 |
| VEGF | 0.00015 |
| TGF-β1 | 0.00002 |

Example 5

Skin Care Composition V

TABLE V

| INGREDIENT | w/w % |
| --- | --- |
| D.I. WATER | Q.S. to 100% |
| ALLANTOIN | 0.10 |
| PANTHENOL | 1.00 |
| BUTYLENE GLYCOL | 2.00 |
| MAGNESIUM ALUMINUM SILICATE | 0.30 |
| XANTHAN GUM | 0.30 |
| GLYCERIN | 3.00 |
| CETEARYL ALCOHOL | 2.50 |
| CETEARETH 20 | |
| GLYCERYL STEARATE | 1.00 |
| SUNFLOWER OIL | 3.50 + 0.50 |
| MEADOWFOAM SEED OIL | 1.00 |
| SHEA BUTTER | 1.00 |
| MANGO BUTTER | 0.50 |
| AVOCADO BUTTER | 0.50 |
| DIMETHICONE | 2.00 |
| LINOLEIC ACID, LINOLENIC ACID, TOCOPHEROL | 0.25 |
| DL-ALPHA TOCOPHERYL ACETATE | 0.001 |
| PHENOXYETHANOL, METHYLPARABEN BUTYLPARABEN PROPYLPARABEN ETHYLPARABEN | 1.00 |
| SODIUM HYALURONATE | 1.00 |
| JAPANESE GREEN TEA EXTRACT | 0.50 |
| METHYLSILANOL MANNURONATE | 1.00 |
| CYCLOPENTASILOXANE | 0.50 |
| DIMETHICONE/VINYL DIMETHICONE CROSSPOLYMER | |
| UBIQUINONE | 0.30 |
| CERAMIDES | 3.00 |
| PEG-40 HYDROGENATED CASTOR OIL | |
| PALMITOYL PENTAPEPTIDE-4 | 3.00 |
| MYRISTOYL PENTAPEPTIDE -8 | 0.50 |
| MYRISTOYL PENTAPEPTIDE -11 | 0.50 |
| ANTIBODY TO HUMAN TELOMERASE REVERSE TRANSCRIPTASE | 0.0006 |
| KGF-1 | 0.00006 |
| VEGF | 0.00015 |
| TGF-β1 | 0.00002 |

Example 6

Skin Care Composition VI

TABLE VI

| INGREDIENT | w/w % |
| --- | --- |
| D.I. WATER | Q.S. to 100% |
| ALLANTOIN | 0.10 |
| PANTHENOL | 1.00 |
| BUTYLENE GLYCOL | 2.00 |
| MAGNESIUM ALUMINUM SILICATE | 0.30 |
| XANTHAN GUM | 0.30 |
| GLYCERIN | 3.00 |
| CETEARYL ALCOHOL | 2.50 |
| CETEARETH 20 | |
| GLYCERYL STEARATE | 1.00 |
| SUNFLOWER OIL | 3.50 + 0.50 |
| MEADOWFOAM SEED OIL | 1.00 |
| SHEA BUTTER | 1.00 |
| MANGO BUTTER | 0.50 |
| AVOCADO BUTTER | 0.50 |
| DIMETHICONE | 2.00 |
| LINOLEIC ACID, LINOLENIC ACID, TOCOPHEROL | 0.25 |
| DL-ALPHA TOCOPHERYL ACETATE | 0.001 |
| PHENOXYETHANOL, METHYLPARABEN BUTYLPARABEN PROPYLPARABEN ETHYLPARABEN | 1.00 |
| SODIUM HYALURONATE | 1.00 |
| JAPANESE GREEN TEA EXTRACT | 0.50 |
| METHYLSILANOL MANNURONATE | 1.00 |
| CYCLOPENTASILOXANE | 0.50 |
| DIMETHICONE/VINYL DIMETHICONE CROSSPOLYMER | |
| UBIQUINONE | 0.30 |
| CERAMIDES | 3.00 |
| PEG-40 HYDROGENATED CASTOR OIL | |
| PALMITOYL PENTAPEPTIDE-4 | 3.00 |
| MYRISTOYL PENTAPEPTIDE -8 | 0.50 |
| MYRISTOYL PENTAPEPTIDE -11 | 0.50 |

TABLE VI-continued

| INGREDIENT | w/w % |
|---|---|
| HUMAN TELOMERASE REVERSE TRANSCRIPTASE | 0.0006 |
| KGF-1 | 0.00006 |
| VEGF | 0.00015 |
| TGF-β1 | 0.00002 |

Example 7

Method of Preparing the Composition of Example 1

The composition of Example 1 is prepared by combining the components of deionized water, allantoin, pathenol, buylene glycol, magnesium aluminum silicate, xanthan gum, and glycerin in the proportions given in Table 1, in a first mixing kettle forming Mixture 1. Mixture 1 is heated to about 70° C. to about 75° C., and mixed until uniform and smooth. In a second mixing kettle, cetearyl alcohol, ceteareth 20, glyceryl stearate, sunflower oil, meadowfoam seed oil, shea butter, mango butter, avocado butter, dimethicone, linoleic acid, linolenic acid, and tocopherol are combined in the proportions given in Table 1, forming Mixture 2. Mixture 2 is heated to about 70° C. to about 75° C. until the mixture is melted completely, and no visible solids remained. After the melting step for Mixture 2 is completed, and both Mixture 1 and Mixture 2 are both at about 70° C. to about 75° C., Mixture 2 is added to Mixture 1 with mixing until the combined Mixture 1 in the first mixing kettle is smooth and uniform. The combined Mixture 1 in the first mixing kettle is then cooled to about 40° C.

Mixture 3, which is made from combining DL-tocopherol acetate, phenoxyethanol, methylparaben, butylparaben, propylparaben, ethylparaben, sodium hyaluronate, Japanese green tea extract, methylsilanol mannuronate, cyclopentasiloxane, and dimethicone/vinyl diemethicone crosspolymer in the proportions given in Table 1, is added to the combined Mixture 1 in the first mixing kettle after combined Mixture 1 is cooled to 40° C. Mixing is continued in the first mixing kettle, until Mixture 1 is uniform and smooth. A group of components including ubiquinone, sunflower oil, ceramides, PEG-40 hydrogenated castor oil, palmitoyl pentapeptide-4, myristoyl pentapeptide-8, and myristoyl pentapeptide-11 are added to Mixture 1 in the first mixing kettle in the proportions given in Table 1, with continued mixing until the augmented Mixture 1 is smooth and uniform. The last addition of components includes human Telomerase RT, KGF-1, EGF, and TGF-β1 in the proportions given in Table 1, which is made to Mixture 1 in the first mixing kettle. Stirring is continued until the composition is smooth and uniform.

Example 8

Method of Preparing the Composition of Example 5

The composition of Example 5 is prepared by combining the components of deionized water, allantoin, pathenol, buylene glycol, magnesium aluminum silicate, xanthan gum, and glycerin in the proportions given in Table 5, in a first mixing kettle forming Mixture 1. Mixture 1 is heated to about 70° C. to about 75° C., and mixed until uniform and smooth. In a second mixing kettle, cetearyl alcohol, ceteareth 20, glyceryl stearate, sunflower oil, meadowfoam seed oil, shea butter, mango butter, avocado butter, dimethicone, linoleic acid, linolenic acid, and tocopherol are combined in the proportions given in Table 5, forming Mixture 2. Mixture 2 is heated to about 70° C. to about 75° C. until the mixture is melted completely, and no visible solids remained. After the melting step for Mixture 2 is completed, and both Mixture 1 and Mixture 2 are both at about 70° C. to about 75° C., Mixture 2 is added to Mixture 1 with mixing until the combined Mixture 1 in the first mixing kettle is smooth and uniform. The combined Mixture 1 in the first mixing kettle is then cooled to about 40° C.

Mixture 3, which is made from combining DL-tocopherol acetate, phenoxyethanol, methylparaben, butylparaben, propylparaben, ethylparaben, sodium hyaluronate, Japanese green tea extract, methylsilanol mannuronate, cyclopentasiloxane, and dimethicone/vinyl diemethicone crosspolymer in the proportions given in Table 5, is added to the combined Mixture 1 in the first mixing kettle after combined Mixture 1 is cooled to 40° C. Mixing is continued in the first mixing kettle, until Mixture 1 is uniform and smooth. A group of components including ubiquinone, sunflower oil, ceramides, PEG-40 hydrogenated castor oil, palmitoyl pentapeptide-4, myristoyl pentapeptide-8, and myristoyl pentapeptide-11 are added to Mixture 1 in the first mixing kettle in the proportions given in Table 5, with continued mixing until the augmented Mixture 1 is smooth and uniform. The last addition of components includes antibody to human Telomerase RT, KGF-1, VEGF, and TGF-β1 in the proportions given in Table 5, which is made to Mixture 1 in the first mixing kettle. Stirring is continued until the composition is smooth and uniform.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for improving the appearance of skin in a human subject, comprising topically applying to the skin of the human subject a composition comprising:
   an Epidermal Growth Factor;
   a Keratinocyte Growth Factor;
   a Transforming Growth factor-beta 1;
   an acylated peptide;
   a coenzyme Q; and
   a cosmetically suitable vehicle;
   wherein applying said composition to the skin of the human subject results in an improvement in the appearance of the skin which is selected from the group consisting of: reduced inflammation of the skin, reduced oxidative stress of the skin, skin brightening, reduced fine lines of the skin, reduced wrinkles of the skin, enhanced elasticity of the skin, and reduced appearance of scarring and lesions.

2. The method of claim 1, wherein the acylated peptide is a palmitoylated peptide.

3. The method of claim 1, wherein the acylated peptide is a myristoylated peptide.

4. The method of claim 1, further comprising a fatty acid.

5. The method of claim 1, further comprising alpha hydroxy acids (AHAs).

6. The method of claim 1, further comprising at least one skin benefit agent selected from the group consisting of at least one humectants, moisturizing agents, and anti-inflammatory agents.

7. The method of claim 1, further comprising an agent which promotes growth of telomeres of cells in the skin.

8. The method of claim 7, wherein the improvement in the appearance of the skin involves prolonging viability of the cells in the skin.

9. The method of claim 1, wherein the composition is applied topically for more than once a day.

10. The method of claim 1, wherein the composition is applied topically for less than six times a week.

* * * * *